US007993841B2

(12) United States Patent
Aasly et al.

(10) Patent No.: US 7,993,841 B2
(45) Date of Patent: Aug. 9, 2011

(54) METHOD OF SCREENING FOR LRRK2-RELATED PARKINSONISM INHERITANCE

(75) Inventors: Jan O Aasly, Trondheim (NO); Zbigniew K Wszolek, Jacksonville, MN (US); Matthew J Farrer, Jacksonville, FL (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 55 days.

(21) Appl. No.: 12/433,385

(22) Filed: Apr. 30, 2009

(65) Prior Publication Data

US 2010/0003685 A1 Jan. 7, 2010

Related U.S. Application Data

(63) Continuation of application No. 10/568,414, filed as application No. PCT/NO2005/000465 on Dec. 19, 2005, now Pat. No. 7,544,786.

(30) Foreign Application Priority Data

Dec. 23, 2004 (NO) .................................. 20045612
May 27, 2005 (NO) .................................. 20052535

(51) Int. Cl.
*C12Q 1/68* (2006.01)
*C12P 19/34* (2006.01)
*C07H 21/04* (2006.01)
*C12N 9/12* (2006.01)

(52) U.S. Cl. .......... 435/6; 435/91.2; 435/194; 536/23.2; 536/23.5; 536/24.31; 536/25.32

(58) Field of Classification Search .................. None
See application file for complete search history.

(56) References Cited

U.S. PATENT DOCUMENTS 6,420,547 B1 7/2002 Maiti et al.

FOREIGN PATENT DOCUMENTS

| WO | WO 02/081627 | 10/2002 |
| WO | WO 2006/045392 | 5/2006 |
| WO | WO 2006/068492 | 6/2006 |

OTHER PUBLICATIONS

Nichols, W. et al. Lancet 365:410-412 (Jan. 2005).*
Brice, A. Lancet 365:363-364 (Jan. 2005).*
DiFonzo, A et al. Lancet 365:412-415 (Jan. 2005).*
GenBank Accession No. AY792511 dated Nov. 15, 2004, 5 pages.
Aasly et al., "Clinical features of LRRK2-associated Parkinson's disease in central Norway," *Ann Neurol*, 2005, 57(5):762-765.
Albrecht, "LRRK2 mutations and Parkinsonism," *Lancet*, 2005, 365:1230.
Bonifati et al., "Mutations in the *DJ-1* Gene Associated with Autosomal Recessive Early-Onset Parkinsonism," *Science*, 2003, 299:256-259.

(Continued)

*Primary Examiner* — Diana Johannsen
(74) *Attorney, Agent, or Firm* — Fish & Richardson P.C.

(57) ABSTRACT

A polynucleotide consisting of the base sequence of SEQ ID NO: 2, or a complementary strand thereto, wherein the X is one of the group being defined by the bases A, C or T. A primer and a probe specific for that polynucleotide, wherein the primer and/or probe contains at the least 10 consecutive nucleotides, and finally use of the probe for proving parkinsonism inheritance.

7 Claims, 6 Drawing Sheets

Probability of becoming affected by parkinsonism, in *LRRK2G2019S* carriers, as a function of age.

OTHER PUBLICATIONS

Bosgraaf and Van Haastert, "Roc, a Ras/GTPase domain in complex proteins," *Biochim Biophys. Acta*, 2003, 1643:5-10.

Chartier-Harlin et al., "α-synuclein locus duplication as a cause of familial Parkinson's disease," *Lancet*, 2004, 364:1167-1169.

Davies et al., "Mutations of the *BRAF* gene in human cancer," *Nature*, 2002, 417:949-954.

de Rijk et al., "Prevalence of Parkinson's disease in the elderly: the Rotterdam Study," *Neurology*, 1995, 45:2143-2146.

Deng et al, "Genetic and clinical identification of Parkinson's disease patients with LRRK2 G2019S mutation," *Ann Neurol*, 2005, 57(6):933-934.

Dibb et al., "Switching on kinases: oncogenic activation of *BRAF* and the *PDGFR* family," *Nat. Rev. Cancer*, 2004, 4:718-727.

Farrer et al., "Comparison of Kindreds with Parkinsonism and α-Synuclein Genomic Multiplications," *Ann. Neurol.*, 2004, 55:174-179.

Forno, "Neuropathology of Parkinson's Disease," *J. Neuropathol. Exp. Neurol.*, 1996, 55(3):259-272.

Funayama et al., "A New Locus for Parkinson's Disease (*PARK8*) Maps to Chromosome 12p11.2-q13.1," *Ann. Neurol.*, 2002, 51:296-301.

Gelb et al., "Diagnostic Criteria for Parkinson Disease," *Arch. Neurol.*, 1999, 56:33-39.

Gilks et al., "Common LRRK2 mutation in idiopathic Parkinson's disease," *Lancet*, 2005, 365:415-416.

Hernandez et al., "Clinical and positron emission tomography of Parkinson's disease caused by LRRK2," *Ann Neurol*, 2005, 57(3):453-456.

Hughes et al., "Accuracy of clinical diagnosis of idiopathic Parkinson''s disease: a clinico-pathological study of 100 cases," *J. Neurol. Neurosurg. Psychiatry*, 1992, 55:181-184.

Huse and Kuriyan, "The Conformational Plasticity of Protein Kinases," *Cell*, 2002, 109:275-282.

Kitada et al., "Mutations in the *parkin* gene cause autosomal recessive juvenile parkinsonism," *Nature*, 1998, 392:605-608.

Kong and Cox, "Allele-Sharing Models: LOD Scores and Accurate Linkage Tests," *Am. J. Hum. Genet.*, 1997, 61:1179-1188.

Krüger et al., "Ala30Pro mutation in the gene encoding α-synuclein in Parkinson's disease," *Nat. Genet.*, 1998, 18:106-108.

Lander and Kruglyak, "Genetic dissection of complex traits: guidelines for interpreting and reporting linkage results," *Nat. Genet.*, 1995, 11:241-247.

Lang and Lozano, "Parkinson's Disease. First of Two Parts," *New Engl. J. Med.*, 1998, 339:1044-1053.

Mata et al., "Parkin genetics: one model for Parkinson's disease," *Hum. Mol. Genet.*, 2004, 13:R127-R133.

Paisán-Ruíz et al., "Cloning of the Gene Containing Mutations that Cause *PARK8*-Linked Parkinson's Disease," *Neuron*, 2004, 44:595-600.

Pals et al., "α-Synuclein Promoter Confers Susceptibility to Parkinson's Disease," *Ann. Neurol.*, 2004, 56:591-595.

Polymeropoulos et al., "Mutation in the α-Synuclein Gene Identified in Families with Parkinson's Disease," *Science*, 1997, 276:2045-2047.

Simon et al., "'Nature versus nurture' and incompletely penetrant mutations," *J. Neurol. Neurosurg. Psychiatry*, 2002, 72:686-688.

Singleton et al., "α-Synuclein Locus Triplication Causes Parkinson's Disease," *Science*, 2003, 302:841.

Slatkin and Rannala, "Estimating allele age," *Annu. Rev. Genomics Hum. Genet.*, 2000, 1:225-249.

Spillantini et al., "α-Synuclein in Lewy bodies," *Nature*, 1997, 388:839-840.

Tanner et al., "Parkinson Disease in Twins: An Etiologic Study," *JAMA*, 1999, 281(4):341-346.

Valente et al., "Hereditary Early-Onset Parkinson's Disease Caused by Mutations in *PINK1*," *Science*, 2004, 304:1158-1160.

Vila and Przedborski, "Genetic clues to the pathogenesis of Parkinson's disease," *Nat. Med.*, 2004, 10(Suppl):S58-S62.

Wirdefeldt et al., "No evidence for heritability of Parkinson disease in Swedish twins," *Neurology*, 2004, 63:305-311.

Zarranz et al., "The New Mutation, E46K, of α-Synuclein Causes Parkinson and Lewy Body Dementia," *Ann. Neurol.*, 2004, 55:164-173.

Zimprich et al., "Mutations in *LRRK2* Cause Autosomal-Dominant Parkinsonism with Pleomorphic Pathology," *Neuron*, 2004, 44:601-607.

Zimprich et al., "The PARK8 locus in autosomal dominant parkinsonism: confirmation of linkage and further delineation of the disease-containing interval," *Am. J. Hum. Genet.*, 2004, 74:11-19.

Zimprich et al., [online], 2004, [retrieved on Nov. 26, 2007]. Retrieved from the Internet:< URL: http://www.ncbi.nlm.nih.gov/entrez/viewer.fcgi?db=nuccore&id=55740397>, pp. 1-5.

Supplementary European Search Report in EP 05 82 3159 mailed Jun. 26, 2009, 10 pages.

* cited by examiner

Figure 2, page 2

Figure 3. Chromosome 12q12 STR markers on the disease haplotype (PARK8).

| Marker | Family proband | | | | | | | | | | |
|---|---|---|---|---|---|---|---|---|---|---|---|
| | P-063 | P-089 | P-104 | P-241 | P-369 | P-394 | F05 | 1210 | 1120 | 111 | 3215 | PD66 | 1P |
| D12S87 | 160 | 160 | 164 | 164 | 122 | 156 | 166 | 156/158 | 164 | 160 | 158 | 156/166 | 166/158 |
| D12S1648 | 120 | 120 | 122 | 122 | 110 | 110 | 110 | 122/124 | 110 | 110 | 110 | 120/134 | 128/130 |
| D12S2080 | 188 | 188 | 188 | 188 | 188 | 188 | 188 | 184/192 | 188 | 180 | 184 | 188/192 | 184/188 |
| D12S2194 | 265 | 265 | 265 | 265 | 265 | 265 | 261 | 253/261 | 257 | 257 | 253 | 245/249 | 249/261 |
| -31Kb | 290 | 290 | 290 | 290 | 290 | 290 | 290 | 280/290 | 290 | 290 | 290 | 290/293 | 284/290 |
| LRRK2_69Kb | 223 | 223 | 223 | 223 | 223 | 223 | 223 | 219/223 | 223 | 223 | 223 | 215/215 | 211/219 |
| LRRK2_84Kb | 253 | 253 | 253 | 253 | 253 | 253 | 253 | 253/253 | 253 | 253 | 253 | 253/253 | 253/253 |
| LRRK2_129Kb | 151 | 151 | 151 | 151 | 151 | 151 | 151 | 151/151 | 151 | 151 | 151 | 151/151 | 151/151 |
| 212Kb | 132 | 132 | 132 | 132 | 132 | 132 | 132 | 132/132 | 132 | 132 | 132/138 | 132/138 | 132/134 |
| 243Kb | 315 | 315 | 315 | 315 | 315 | 315 | 315 | 315/315 | 315 | 315 | 315/309 | 315/312 | 315/300 |
| 378Kb | 189 | 189 | 189 | 189 | 189 | 189 | 189 | 189/193 | 193 | 193 | 191 | 183/189 | 183/187 |
| D12S1048 | 214 | 214 | 214 | 214 | 214 | 211/214 | 214 | 214/223 | 214 | 214 | 223 | 211/214 | 211/226 |
| D12S1301 | 112 | 116 | 120 | 120 | 116 | 116 | 116 | 108/116 | 100 | 120 | 116 | 100/116 | 100/100 |
| D12S1701 | 95 | 97 | 91 | 91 | 95 | 95/97 | 97 | 95/101 | 92 | 91/95 | 95 | 97/101 | 91/97 |
| Country of origin | Norway | | | | | | United States | | | | Ireland | Poland |

Genotypes for probands from 13 families with *LRRK2* G2019S are shown; those shared are highlighted in grey.

Figure 4. Probability of becoming affected by parkinsonism, in *LRRK2*G2019S carriers, as a function of age.

Figure 5

| | | |
|---|---|---|
| LRRK2 | DYGIAQ------YCCRMGIKTSEGTPGFRAPE |
| LRRK1 | DYGISR------QSFHEGALGVEGTPGYQAPE |
| MATK | DPGLAK------AEREGLDSSRLPVKWTAPE |
| PDGFRA | DFGLARDIMHDSNYVSKGSTFLPVKWMAPE |
| MAP3K10 | QFGIAR------EWHKTTKMSAAGTYAWMAPE |
| DAPK1 | DFGN---------EFKNIFGTPEFVAPE |
| BRAP | DFGLATVKSRWSGSEQEQLSGSILWMAPE |

SEQUENCE LISTING

```
<160> NUMBER OF SEQ ID NOS: 25

<210> SEQ ID NO 1
<211> LENGTH: 2527
<212> TYPE: PRT
<213> ORGANISM: Homo sapiens
<220> FEATURE:
<221> NAME/KEY: VARIANT
<222> LOCATION: 2019
<223> OTHER INFORMATION: Xaa = Any Amino Acid

<400> SEQUENCE: 1

Met Ala Ser Gly Ser Cys Gln Gly Cys Glu Glu Asp Glu Glu Thr Leu
 1               5                  10                  15

Lys Lys Leu Ile Val Arg Leu Asn Asn Val Gln Glu Gly Lys Gln Ile
                20                  25                  30

Glu Thr Leu Val Gln Ile Leu Glu Asp Leu Leu Val Phe Thr Tyr Ser
            35                  40                  45

Glu His Ala Ser Lys Leu Phe Gln Gly Lys Asn Ile His Val Pro Leu
        50                  55                  60

Leu Ile Val Leu Asp Ser Tyr Met Arg Val Ala Ser Val Gln Gln Val
 65                  70                  75                  80

Gly Trp Ser Leu Leu Cys Lys Leu Ile Glu Val Cys Pro Gly Thr Met
                85                  90                  95

Gln Ser Leu Met Gly Pro Gln Val Gly Asn Asp Trp Glu Val Leu
                100                 105                 110

Gly Val His Gln Leu Ile Leu Lys Met Leu Thr Val His Asn Ala Ser
            115                 120                 125

Val Asn Leu Ser Val Ile Gly Leu Lys Thr Leu Asp Leu Leu Leu Thr
        130                 135                 140

Ser Gly Lys Ile Thr Leu Leu Ile Leu Asp Glu Glu Ser Asp Ile Phe
145                 150                 155                 160

Met Leu Ile Phe Asp Ala Met His Ser Phe Pro Ala Asn Asp Glu Val
                165                 170                 175

Gln Lys Leu Gly Cys Lys Ala Leu His Val Leu Phe Glu Arg Val Ser
            180                 185                 190
```

```
Glu Glu Gln Leu Thr Glu Phe Val Glu Asn Lys Asp Tyr Met Ile Leu
            195                 200                 205
Leu Ser Ala Ser Thr Asn Phe Lys Asp Glu Glu Ile Val Leu His
210                 215                 220
Val Leu His Cys Leu His Ser Leu Ala Ile Pro Cys Asn Asn Val Glu
225                 230                 235                 240
Val Leu Met Ser Gly Asn Val Arg Cys Tyr Asn Ile Val Val Glu Ala
                245                 250                 255
Met Lys Ala Phe Pro Met Ser Glu Arg Ile Gln Glu Val Ser Cys Cys
            260                 265                 270
Leu Leu His Arg Leu Thr Leu Gly Asn Phe Asn Ile Leu Val Leu
            275                 280                 285
Asn Glu Val His Glu Phe Val Val Lys Ala Val Gln Gln Tyr Pro Glu
            290                 295                 300
Asn Ala Ala Leu Gln Ile Ser Ala Leu Ser Cys Leu Ala Leu Leu Thr
305                 310                 315                 320
Glu Thr Ile Phe Leu Asn Gln Asp Leu Glu Glu Lys Asn Glu Asn Gln
                325                 330                 335
Glu Asn Asp Asp Glu Gly Glu Glu Asp Lys Leu Phe Trp Leu Glu Ala
                340                 345                 350
Cys Tyr Lys Ala Leu Thr Trp His Arg Lys Asn Lys His Val Gln Glu
            355                 360                 365
Ala Ala Cys Trp Ala Leu Asn Asn Leu Leu Met Tyr Gln Asn Ser Leu
            370                 375                 380
His Glu Lys Ile Gly Asp Glu Asp Gly His Phe Pro Ala His Arg Glu
385                 390                 395                 400
Val Met Leu Ser Met Leu Met His Ser Ser Lys Glu Val Phe Gln
                405                 410                 415
Ala Ser Ala Asn Ala Leu Ser Thr Leu Leu Glu Gln Asn Val Asn Phe
            420                 425                 430
Arg Lys Ile Leu Leu Ser Lys Gly Ile His Leu Asn Val Leu Glu Leu
            435                 440                 445
Met Gln Lys His Ile His Ser Pro Glu Val Ala Glu Ser Gly Cys Lys
            450                 455                 460
Met Leu Asn His Leu Phe Glu Gly Ser Asn Thr Ser Leu Asp Ile Met
465                 470                 475                 480
Ala Ala Val Val Pro Lys Ile Leu Thr Val Met Lys Arg His Glu Thr
                485                 490                 495
Ser Leu Pro Val Gln Leu Glu Ala Leu Arg Ala Ile Leu His Phe Ile
            500                 505                 510
Val Pro Gly Met Pro Glu Glu Ser Arg Glu Asp Thr Glu Phe His His
            515                 520                 525
Lys Leu Asn Met Val Lys Lys Gln Cys Phe Lys Asn Asp Ile His Lys
530                 535                 540
Leu Val Leu Ala Ala Leu Asn Arg Phe Ile Gly Asn Pro Gly Ile Gln
545                 550                 555                 560
Lys Cys Gly Leu Lys Val Ile Ser Ser Ile Val His Phe Pro Asp Ala
                565                 570                 575
Leu Glu Met Leu Ser Leu Glu Gly Ala Met Asp Ser Val Leu His Thr
            580                 585                 590
Leu Gln Met Tyr Pro Asp Asp Gln Glu Ile Gln Cys Leu Gly Leu Ser
            595                 600                 605
Leu Ile Gly Tyr Leu Ile Thr Lys Lys Asn Val Phe Ile Gly Thr Gly
```

-continued

```
            610                 615                 620
His Leu Ala Lys Ile Leu Val Ser Ser Leu Tyr Arg Phe Lys Asp
625                 630                 635                 640

Val Ala Glu Ile Gln Thr Lys Gly Phe Gln Thr Ile Leu Ala Ile Leu
                    645                 650                 655

Lys Leu Ser Ala Ser Phe Ser Lys Leu Leu Val His Ser Phe Asp
                660                 665                 670

Leu Val Ile Phe His Gln Met Ser Ser Asn Ile Met Glu Gln Lys Asp
                675                 680                 685

Gln Gln Phe Leu Asn Leu Cys Cys Lys Cys Phe Ala Lys Val Ala Met
690                 695                 700

Asp Asp Tyr Leu Lys Asn Val Met Leu Glu Arg Ala Cys Asp Gln Asn
705                 710                 715                 720

Asn Ser Ile Met Val Glu Cys Leu Leu Leu Gly Ala Asp Ala Asn
                    725                 730                 735

Gln Ala Lys Glu Gly Ser Ser Leu Ile Cys Gln Val Cys Glu Lys Glu
                740                 745                 750

Ser Ser Pro Lys Leu Val Glu Leu Leu Asn Ser Gly Ser Arg Glu
                755                 760                 765

Gln Asp Val Arg Lys Ala Leu Thr Ile Ser Ile Gly Lys Gly Asp Ser
770                 775                 780

Gln Ile Ile Ser Leu Leu Arg Arg Leu Ala Leu Asp Val Ala Asn
785                 790                 795                 800

Asn Ser Ile Cys Leu Gly Gly Phe Cys Ile Gly Lys Val Glu Pro Ser
                    805                 810                 815

Trp Leu Gly Pro Leu Phe Pro Asp Lys Thr Ser Asn Leu Arg Lys Gln
                820                 825                 830

Thr Asn Ile Ala Ser Thr Leu Ala Arg Met Val Ile Arg Tyr Gln Met
                835                 840                 845

Lys Ser Ala Val Glu Gly Thr Ala Ser Gly Ser Asp Gly Asn Phe
850                 855                 860

Ser Glu Asp Val Leu Ser Lys Phe Asp Glu Trp Thr Phe Ile Pro Asp
865                 870                 875                 880

Ser Ser Met Asp Ser Val Phe Ala Gln Ser Asp Asp Leu Asp Ser Glu
                    885                 890                 895

Gly Ser Glu Gly Ser Phe Leu Val Lys Lys Ser Asn Ser Ile Ser
                900                 905                 910

Val Gly Glu Phe Tyr Arg Asp Ala Val Leu Gln Arg Cys Ser Pro Asn
                915                 920                 925

Leu Gln Arg His Ser Asn Ser Leu Gly Pro Ile Phe Asp His Glu Asp
930                 935                 940

Leu Leu Lys Arg Lys Arg Lys Ile Leu Ser Ser Asp Asp Ser Leu Arg
945                 950                 955                 960

Ser Ser Lys Leu Gln Ser His Met Arg His Ser Asp Ser Ile Ser Ser
                    965                 970                 975

Leu Ala Ser Glu Arg Glu Tyr Ile Thr Ser Leu Asp Leu Ser Ala Asn
                980                 985                 990

Glu Leu Arg Asp Ile Asp Ala Leu Ser Gln Lys Cys Cys Ile Ser Val
                995                 1000                1005

His Leu Glu His Leu Glu Lys Leu Glu Leu His Gln Asn Ala Leu Thr
                    1010                1015                1020

Ser Phe Pro Gln Gln Leu Cys Glu Thr Leu Lys Ser Leu Thr His Leu
1025                1030                1035                1040
```

-continued

Asp Leu His Ser Asn Lys Phe Thr Ser Phe Pro Ser Tyr Leu Leu Lys
            1045                1050                1055

Met Ser Cys Ile Ala Asn Leu Asp Val Ser Arg Asn Asp Ile Gly Pro
            1060                1065                1070

Ser Val Val Leu Asp Pro Thr Val Lys Cys Pro Thr Leu Lys Gln Phe
            1075                1080                1085

Asn Leu Ser Tyr Asn Gln Leu Ser Phe Val Pro Glu Asn Leu Thr Asp
            1090                1095                1100

Val Val Glu Lys Leu Glu Gln Leu Ile Leu Glu Gly Asn Lys Ile Ser
1105                1110                1115                1120

Gly Ile Cys Ser Pro Leu Arg Leu Lys Glu Leu Lys Ile Leu Asn Leu
            1125                1130                1135

Ser Lys Asn His Ile Ser Ser Leu Ser Glu Asn Phe Leu Glu Ala Cys
            1140                1145                1150

Pro Lys Val Glu Ser Phe Ser Ala Arg Met Asn Phe Leu Ala Ala Met
            1155                1160                1165

Pro Phe Leu Pro Pro Ser Met Thr Ile Leu Lys Leu Ser Gln Asn Lys
            1170                1175                1180

Phe Ser Cys Ile Pro Glu Ala Ile Leu Asn Leu Pro His Leu Arg Ser
1185                1190                1195                1200

Leu Asp Met Ser Ser Asn Asp Ile Gln Tyr Leu Pro Gly Pro Ala His
            1205                1210                1215

Trp Lys Ser Leu Asn Leu Arg Glu Leu Leu Phe Ser His Asn Gln Ile
            1220                1225                1230

Ser Ile Leu Asp Leu Ser Glu Lys Ala Tyr Leu Trp Ser Arg Val Glu
            1235                1240                1245

Lys Leu His Leu Ser His Asn Lys Leu Lys Glu Ile Pro Pro Glu Ile
            1250                1255                1260

Gly Cys Leu Glu Asn Leu Thr Ser Leu Asp Val Ser Tyr Asn Leu Glu
1265                1270                1275                1280

Leu Arg Ser Phe Pro Asn Glu Met Gly Lys Leu Ser Lys Ile Trp Asp
            1285                1290                1295

Leu Pro Leu Asp Glu Leu His Leu Asn Phe Asp Phe Lys His Ile Gly
            1300                1305                1310

Cys Lys Ala Lys Asp Ile Ile Arg Phe Leu Gln Gln Arg Leu Lys Lys
            1315                1320                1325

Ala Val Pro Tyr Asn Arg Met Lys Leu Met Ile Val Gly Asn Thr Gly
            1330                1335                1340

Ser Gly Lys Thr Thr Leu Leu Gln Gln Leu Met Lys Thr Lys Lys Ser
1345                1350                1355                1360

Asp Leu Gly Met Gln Ser Ala Thr Val Gly Ile Asp Val Lys Asp Trp
            1365                1370                1375

Pro Ile Gln Ile Arg Asp Lys Arg Lys Arg Asp Leu Val Leu Asn Val
            1380                1385                1390

Trp Asp Phe Ala Gly Arg Glu Glu Phe Tyr Ser Thr His Pro His Phe
            1395                1400                1405

Met Thr Gln Arg Ala Leu Tyr Leu Ala Val Tyr Asp Leu Ser Lys Gly
            1410                1415                1420

Gln Ala Glu Val Asp Ala Met Lys Pro Trp Leu Phe Asn Ile Lys Ala
1425                1430                1435                1440

Arg Ala Ser Ser Ser Pro Val Ile Leu Val Gly Thr His Leu Asp Val
            1445                1450                1455

Ser Asp Glu Lys Gln Arg Lys Ala Cys Met Ser Lys Ile Thr Lys Glu
            1460                1465                1470

```
Leu Leu Asn Lys Arg Gly Phe Pro Ala Ile Arg Asp Tyr His Phe Val
        1475                1480                1485

Asn Ala Thr Glu Glu Ser Asp Ala Leu Ala Lys Leu Arg Lys Thr Ile
        1490                1495                1500

Ile Asn Glu Ser Leu Asn Phe Lys Ile Arg Asp Gln Leu Val Val Gly
1505                1510                1515                1520

Gln Leu Ile Pro Asp Cys Tyr Val Leu Glu Lys Ile Ile Leu Ser
            1525                1530                1535

Glu Arg Lys Asn Val Pro Ile Glu Phe Pro Val Ile Asp Arg Lys Arg
            1540                1545                1550

Leu Leu Gln Leu Val Arg Glu Asn Gln Leu Gln Leu Asp Glu Asn Glu
        1555                1560                1565

Leu Pro His Ala Val His Phe Leu Asn Glu Ser Gly Val Leu Leu His
        1570                1575                1580

Phe Gln Asp Pro Ala Leu Gln Leu Ser Asp Leu Tyr Phe Val Glu Pro
1585                1590                1595                1600

Lys Trp Leu Cys Lys Ile Met Ala Gln Ile Leu Thr Val Lys Val Glu
            1605                1610                1615

Gly Cys Pro Lys His Pro Lys Gly Ile Ile Ser Arg Arg Asp Val Glu
            1620                1625                1630

Lys Phe Leu Ser Lys Lys Arg Lys Phe Pro Lys Asn Tyr Met Ser Gln
            1635                1640                1645

Tyr Phe Lys Leu Leu Glu Lys Phe Gln Ile Ala Leu Pro Ile Gly Glu
            1650                1655                1660

Glu Tyr Leu Leu Val Pro Ser Ser Leu Ser Asp His Arg Pro Val Ile
1665                1670                1675                1680

Glu Leu Pro His Cys Glu Asn Ser Glu Ile Ile Ile Arg Leu Tyr Glu
            1685                1690                1695

Met Pro Tyr Phe Pro Met Gly Phe Trp Ser Arg Leu Ile Asn Arg Leu
            1700                1705                1710

Leu Glu Ile Ser Pro Tyr Met Leu Ser Gly Arg Glu Arg Ala Leu Arg
            1715                1720                1725

Pro Asn Arg Met Tyr Trp Arg Gln Gly Ile Tyr Leu Asn Trp Ser Pro
            1730                1735                1740

Glu Ala Tyr Cys Leu Val Gly Ser Glu Val Leu Asp Asn His Pro Glu
1745                1750                1755                1760

Ser Phe Leu Lys Ile Thr Val Pro Ser Cys Arg Lys Gly Cys Ile Leu
            1765                1770                1775

Leu Gly Gln Val Val Asp His Ile Asp Ser Leu Met Glu Glu Trp Phe
            1780                1785                1790

Pro Gly Leu Leu Glu Ile Asp Ile Cys Gly Glu Gly Thr Leu Leu
            1795                1800                1805

Lys Lys Trp Ala Leu Tyr Ser Phe Asn Asp Gly Glu Glu His Gln Lys
        1810                1815                1820

Ile Leu Leu Asp Asp Leu Met Lys Lys Ala Glu Glu Gly Asp Leu Leu
1825                1830                1835                1840

Val Asn Pro Asp Gln Pro Arg Leu Thr Ile Pro Ile Ser Gln Ile Ala
            1845                1850                1855

Pro Asp Leu Ile Leu Ala Asp Leu Pro Arg Asn Ile Met Leu Asn Asn
            1860                1865                1870

Asp Glu Leu Glu Phe Glu Gln Ala Pro Glu Phe Leu Leu Gly Asp Gly
            1875                1880                1885

Ser Phe Gly Ser Val Tyr Arg Ala Ala Tyr Glu Gly Glu Glu Val Ala
```

```
                1890              1895              1900
Val Lys Ile Phe Asn Lys His Thr Ser Leu Arg Leu Arg Gln Glu
1905            1910              1915              1920

Leu Val Val Leu Cys His Leu His Pro Ser Leu Ile Ser Leu Leu
                1925              1930              1935

Ala Ala Gly Ile Arg Pro Arg Met Leu Val Met Glu Leu Ala Ser Lys
                1940              1945              1950

Gly Ser Leu Asp Arg Leu Leu Gln Gln Asp Lys Ala Ser Leu Thr Arg
                1955              1960              1965

Thr Leu Gln His Arg Ile Ala Leu His Val Ala Asp Gly Leu Arg Tyr
                1970              1975              1980

Leu His Ser Ala Met Ile Ile Tyr Arg Asp Leu Lys Pro His Asn Val
1985            1990              1995              2000

Leu Leu Phe Thr Leu Tyr Pro Asn Ala Ala Ile Ala Lys Ile Ala
                2005              2010              2015

Asp Tyr Xaa Ile Ala Gln Tyr Cys Cys Arg Met Gly Ile Lys Thr Ser
                2020              2025              2030

Glu Gly Thr Pro Gly Phe Arg Ala Pro Glu Val Ala Arg Gly Asn Val
                2035              2040              2045

Ile Tyr Asn Gln Gln Ala Asp Val Tyr Ser Phe Gly Leu Leu Leu Tyr
                2050              2055              2060

Asp Ile Leu Thr Thr Gly Gly Arg Ile Val Glu Gly Leu Lys Phe Pro
2065            2070              2075              2080

Asn Glu Phe Asp Glu Leu Glu Ile Gln Gly Lys Leu Pro Asp Pro Val
                2085              2090              2095

Lys Glu Tyr Gly Cys Ala Pro Trp Pro Met Val Glu Lys Leu Ile Lys
                2100              2105              2110

Gln Cys Leu Lys Glu Asn Pro Gln Glu Arg Pro Thr Ser Ala Gln Val
                2115              2120              2125

Phe Asp Ile Leu Asn Ser Ala Glu Leu Val Cys Leu Thr Arg Arg Ile
                2130              2135              2140

Leu Leu Pro Lys Asn Val Ile Val Glu Cys Met Val Ala Thr His His
2145            2150              2155              2160

Asn Ser Arg Asn Ala Ser Ile Trp Leu Gly Cys Gly His Thr Asp Arg
                2165              2170              2175

Gly Gln Leu Ser Phe Leu Asp Leu Asn Thr Glu Gly Tyr Thr Ser Glu
                2180              2185              2190

Glu Val Ala Asp Ser Arg Ile Leu Cys Leu Ala Leu Val His Leu Pro
                2195              2200              2205

Val Glu Lys Glu Ser Trp Ile Val Ser Gly Thr Gln Ser Gly Thr Leu
                2210              2215              2220

Leu Val Ile Asn Thr Glu Asp Gly Lys Lys Arg His Thr Leu Glu Lys
2225            2230              2235              2240

Met Thr Asp Ser Val Thr Cys Leu Tyr Cys Asn Ser Phe Ser Lys Gln
                2245              2250              2255

Ser Lys Gln Lys Asn Phe Leu Leu Val Gly Thr Ala Asp Gly Lys Leu
                2260              2265              2270

Ala Ile Phe Glu Asp Lys Thr Val Lys Leu Lys Gly Ala Ala Pro Leu
                2275              2280              2285

Lys Ile Leu Asn Ile Gly Asn Val Ser Thr Pro Leu Met Cys Leu Ser
                2290              2295              2300

Glu Ser Thr Asn Ser Thr Glu Arg Asn Val Met Trp Gly Gly Cys Gly
2305            2310              2315              2320
```

-continued

```
Thr Lys Ile Phe Ser Phe Ser Asn Asp Phe Thr Ile Gln Lys Leu Ile
            2325                2330                2335

Glu Thr Arg Thr Ser Gln Leu Phe Ser Tyr Ala Ala Phe Ser Asp Ser
            2340                2345                2350

Asn Ile Ile Thr Val Val Val Asp Thr Ala Leu Tyr Ile Ala Lys Gln
            2355                2360                2365

Asn Ser Pro Val Val Glu Val Trp Asp Lys Lys Thr Glu Lys Leu Cys
            2370                2375                2380

Gly Leu Ile Asp Cys Val His Phe Leu Arg Glu Val Met Val Lys Glu
2385                2390                2395                2400

Asn Lys Glu Ser Lys His Lys Met Ser Tyr Ser Gly Arg Val Lys Thr
            2405                2410                2415

Leu Cys Leu Gln Lys Asn Thr Ala Leu Trp Ile Gly Thr Gly Gly Gly
            2420                2425                2430

His Ile Leu Leu Leu Asp Leu Ser Thr Arg Arg Leu Ile Arg Val Ile
            2435                2440                2445

Tyr Asn Phe Cys Asn Ser Val Arg Val Met Met Thr Ala Gln Leu Gly
            2450                2455                2460

Ser Leu Lys Asn Val Met Leu Val Leu Gly Tyr Asn Arg Lys Asn Thr
2465                2470                2475                2480

Glu Gly Thr Gln Lys Gln Lys Glu Ile Gln Ser Cys Leu Thr Val Trp
            2485                2490                2495

Asp Ile Asn Leu Pro His Glu Val Gln Asn Leu Glu Lys His Ile Glu
            2500                2505                2510

Val Arg Lys Glu Leu Ala Glu Lys Met Arg Arg Thr Ser Val Glu
            2515                2520                2525

<210> SEQ ID NO 2
<211> LENGTH: 7584
<212> TYPE: DNA
<213> ORGANISM: Homo sapiens
<220> FEATURE:
<221> NAME/KEY: misc_feature
<222> LOCATION: 149, 3364, 4321, 5096, 5457, 6055
<223> OTHER INFORMATION: n = A,T,C or G

<400> SEQUENCE: 2
atggctagtg gcagctgtca ggggtgcgaa gaggacgagg aaactctgaa gaagttgata      60
gtcaggctga acaatgtcca ggaaggaaaa cagatagaaa cgctggtcca aatcctggag     120
gatctgctgg tgttcacgta ctccgagcnc gcctccaagt tatttcaagg caaaaatatc     180
catgtgcctc tgttgatcgt cttggactcc tatatgagag tcgcgagtgt gcagcaggtg     240
ggttggtcac ttctgtgcaa attaatagaa gtctgtccag gtacaatgca aagcttaatg     300
ggaccccagg atgttggaaa tgattgggaa gtccttggtg ttcaccaatt gattcttaaa     360
atgctaacag ttcataatgc cagtgtaaac ttgtcagtga ttggactgaa gaccttagat     420
ctcctcctaa cttcaggtaa aatcaccttg ctgatactgg atgaagaaag tgatattttc     480
atgttaattt tgatgccat gcactcattt ccagccaatg atgaagtcca gaaacttgga     540
tgcaaagctt acatgtgct gtttgagaga gtctcagagg agcaactgac tgaatttgtt     600
gagaacaaag attatatgat attgttaagt gcgtcaacaa attttaaaga tgaagaggaa     660
attgtgcttc atgtgctgca ttgtttacat tccctacgca ttccttgcaa taatgtggaa     720
gtcctcatga gtggcaatgt caggtgttat aatattgtgg tggaagctat gaaagcattc     780
cctatgagtc aaagaattca agaagtgagt tgctgtgttt gctccatagg ct acattaggt     840 aatttttttca atatcctggt attaaacgaa gtccatgagt ttgtggtgaa agctgtgcag     900
```

```
cagtacccag agaatgcagc attgcagatc tcagcgctca gctgtttggc cctcctcact    960
gagactattt tcttaaatca agatttagag gaaagaatg agaatcaaga gaatgatgat   1020 gaggggaag aagataaatt gttttggctg gaagcctgtt acaaagcatt aacgtggcat   1080
agaaagaaca agcacgtgca ggaggccgca tgctgggcac taaataatct ccttatgtac   1140
caaaacagtt tacatgagaa gattggagat gaagatggcc atttcccagc tcatagggaa   1200
gtgatgctct ccatgctgat gcattcttca tcaaggaag ttttccaggc atctgcgaat   1260
gcattgtcaa ctctcttaga acaaaatgtt aatttcagaa aaatactgtt atcaaaagga   1320
atacacctga atgttttgga gttaatgcag aagcatatac attctcctga agtggctgaa   1380
agtggctgta aaatgctaaa tcatcttttt gaaggaagca cacttccct ggatataatg   1440 gcagcagtgg tccccaaaat actaacagtt atgaaacgtc atgagacatc attaccagtg   1500
cagctggagg cgcttcgagc tattttacat tttatagtgc ctggcatgcc agaagaatcc   1560
agggaggata cagaatttca tcataagcta aatatggtta aaaaacagtg tttcaagaat   1620
gatattcaca aactggtcct agcagctttg aacaggttca ttggaaatcc tgggattcag   1680 aaaatgtggat taaaagtaat ttcttctatt gtacattttc ctgatgcatt agagatgtta   1740
tccctggaag gtgctatgga ttcagtgctt cacacactgc agatgtatcc agatgaccaa   1800
gaaattcagt gtctgggttt aagtcttata ggatacttga ttacaaagaa gaatgtgttc   1860
ataggaactg gacatctgct ggcaaaaatt ctggtttcca gcttataccg atttaaggat   1920
gttgctgaaa tacagactaa aggatttcag acaatcttag caatcctcaa attgtcagca   1980 tcttttcta agctgctggt gcatcattca tttgacttag taatattcca tcaaatgtct   2040
tccaatatca tggaacaaaa ggatcaacag tttctaaacc tctgttgcaa gtgttttgca   2100
aaagtagcta tggatgatta cttaaaaaat gtgatgctag agagagcgtg tgatcagaat   2160
aacagcatca tggttgaatg cttgcttcta ttgggagcag atgccaatca agcaaaggag   2220
ggatcttctt taatttgtca ggtatgtgag aaagagagca gtcccaaatt ggtggaactc   2280
ttactgaata gtggatctcg tgaacaagat gtacgaaaag cgttgacgat aagcattggg   2340
aaaggtgaca gccagatcat cagcttgctc ttaaggaggc tggccctgga tgtggccaac   2400
aatagcattt gccttggagg attttgtata ggaaaagttg aaccttcttg gcttggtcct   2460
ttatttccag ataagacttc taatttaagg aaacaaacaa atatagcatc tacactagca   2520
agaatggtga tcagatatca gatgaaaagt gctgtggaag aaggaacagc ctcaggcagc   2580
gatggaaatt tttctgaaga tgtgctgtct aaatttgatg aatggacctt tattcctgac   2640
tcttctatgg acagtgtgtt tgctcaaagt gatgacctgg atagtgaagg aagtgaaggc   2700
tcatttcttg tgaaaagaa atctaattca attagtgtag gagaattta ccgagatgcc   2760 gtattacagc gttgctcacc aaatttgcaa agacattcca attccttggg gcccattttt   2820
gatcatgaag atttactgaa gcgaaaaga aaaatactat cttcagatga ttcactcagg   2880
tcatcaaaac ttcaatccca tatgaggcat tcagacagca tttcttctct ggcttctgag   2940
agagaatata ttacatcact agacctttca gcaaatgaac taagagatat tgatgcccta   3000
agccagaaat gctgtataag tgttcatttg gagcatcttg aaaagctgga gcttcaccag   3060
aatgcactca cgagctttcc acaacagcta tgtgaaactc tgaagagttt gacacatttg   3120
gacttgcaca gtaataaatt tacatcattt ccttcttatt tgttgaaaat gagttgtatt   3180
gctaatcttg atgtctctcg aaatgacatt ggaccctcag tggttttaga tcctacagtg   3240
aaatgtccaa ctctgaaaca gtttaacctg tcatataacc agctgtcttt tgtacctgag   3300
```

```
aacctcactg atgtggtaga gaaactggag cagctcattt tagaaggaaa taaaatatca    3360
gggntatgct cccccttgag actgaaggaa ctgaagattt taaaccttag taagaaccac    3420
atttcatccc tatcagagaa ctttcttgag gcttgtccta aagtggagag tttcagtgcc    3480
agaatgaatt ttcttgctgc tatgccttc ttgcctcctt ctatgacaat cctaaaatta    3540
tctcagaaca aattttcctg tattccagaa gcaattttaa atcttccaca cttgcggtct    3600
ttagatatga gcagcaatga tattcagtac ctaccaggtc ccgcacactg gaaatctttg    3660
aacttaaggg aactcttatt tagccataat cagatcagca tcttggactt gagtgaaaaa    3720
gcatatttat ggtctagagt agagaaactg catctttctc acaataaact gaaagagatt    3780
cctcctgaga ttggctgtct tgaaaatctg acatctctgg atgtcagtta caacttggaa    3840
ctaagatcct ttcccaatga aatggggaaa ttaagcaaaa tatgggatct tcctttggat    3900
gaactgcatc ttaactttga ttttaaacat ataggatgta aagccaaaga catcataagg    3960
tttcttcaac agcgattaaa aaaggctgtg ccttataacc gaatgaaact tatgattgtg    4020
ggaaatactg ggagtggtaa aaccaccta ttgcagcaat taatgaaaac caagaaatca    4080
gatcttggaa tgcaaagtgc cacagttggc atagatgtga aagactggcc tatccaaata    4140
agagacaaaa gaaagagaga tctcgtccta aatgtgtggg attttgcagg tcgtgaggaa    4200
ttctatagta ctcatcccca ttttatgacg cagcgagcat tgtaccttgc tgtctatgac    4260
ctcagcaagg gacaggctga agttgatgcc atgaagcctt ggctcttcaa tataaaggct    4320
ngcgcttctt cttcccctgt gattctcgtt ggcacacatt tggatgtttc tgatgagaag    4380
caacgcaaag cctgcatgag taaaatcacc aaggaactcc tgaataagcg agggttccct    4440
gccatacgag attccactt tgtgaatgcc accgaggaat ctgatgcttt ggcaaaactt    4500
cggaaaacca tcataaacga gagccttaat ttcaagatcc gagatcagct tgttgttgga    4560
cagctgattc cagactgcta tgtagaactt gaaaaaatca ttttatcgga gcgtaaaaat    4620
gtgccaattg aatttcccgt aattgaccgg aaacgattat tacaactagt gagagaaaat    4680
cagctgcagt tagatgaaaa tgagcttcct cacgcagttc actttctaaa tgaatcagga    4740
gtccttcttc attttcaaga cccagcactg cagttaagtg acttgtactt tgtggaaccc    4800
aagtggcttt gtaaaatcat ggcacagatt ttgacagtga aagtggaagg ttgtccaaaa    4860
caccctaagg gcattatttc gcgtagagat gtggaaaaat ttctttcaaa aaaaaggaaa    4920
tttccaaaga actacatgtc acagtatttt aagctcctag aaaaattcca gattgctttg    4980
ccaataggag aagaatattt gctggttcca agcagtttgt ctgaccacag gcctgtgata    5040
gagcttcccc attgtgagaa ctctgaaatt atcatccgac tatatgaaat gccttntttt    5100
ccaatgggat tttggtcaag attaatcaat cgattacttg agatttcacc ttacatgctt    5160
tcagggagag aacgagcact tcgcccaaac agaatgtatt ggcgacaagg catttactta    5220
aattggtctc ctgaagctta ttgtctggta ggatctgaag tcttagacaa tcatccagag    5280
agtttcttaa aaattacagt tccttcttgt agaaaaggct gtattctttt gggccaagtt    5340
gtggaccaca ttgattctct catggaagaa tggtttcctg ggttgctgga gattgatatt    5400
tgtggtgaag gagaaactct gttgaagaaa tgggcattat atagtttttaa tgatggngaa    5460 gaacatcaaa aaatcttact tgatgacttg atgaagaaag cagaggaagg agatctctta    5520
gtaaatccag atcaaccaag gctcaccatt ccaatatctc agattgcccc tgacttgatt    5580
ttggctgacc tgcctagaaa tattatgttg aataatgatg agttggaatt tgaacaagct    5640
ccagagtttc tcctaggtga tggcagtttt ggatcagttt accgagcagc ctatgaagga    5700
```

```
gaagaagtgg ctgtgaagat ttttaataaa catacatcac tcaggctgtt aagacaagag    5760
cttgtggtgc tttgccacct ccaccacccc agtttgatat ctttgctggc agctgggatt    5820
cgtccccgga tgttggtgat ggagttagcc tccaagggtt ccttggatcg cctgcttcag    5880
caggacaaag ccagcctcac tagaacccta cagcacagga ttgcactcca cgtagctgat    5940
ggtttgagat acctccactc agccatgatt atataccgag acctgaaacc ccacaatgtg    6000
ctgcttttca cactgtatcc caatgctgcc atcattgcaa agattgctga ctacngcatt    6060
gctcagtact gctgtagaat ggggataaaa acatcagagg gcacaccagg gtttcgtgca    6120
cctgaagttg ccagaggaaa tgtcatttat aaccaacagg ctgatgttta ttcatttggt    6180
ttactactct atgacatttt gacaactgga ggtagaatag tagagggttt gaagtttcca    6240
aatgagtttg atgaattaga aatacaagga aaattacctg atccagttaa agaatatggt    6300
tgtgccccat ggcctatggt tgagaaatta attaaacagt gtttgaaaga aaatcctcaa    6360
gaaaggccta cttctgccca ggtctttgac attttgaatt cagctgaatt agtctgtctg    6420
acgagacgca ttttattacc taaaaacgta attgttgaat gcatggttgc tacacatcac    6480
aacagcagga atgcaagcat ttggctgggc tgtgggcaca ccgacagagg acagctctca    6540
tttcttgact taaatactga aggatacact tctgaggaag ttgctgatag tagaatattg    6600
tgcttagcct tggtgcatct tcctgttgaa aaggaaagct ggattgtgtc tgggacacag    6660
tctggtactc tcctggtcat caataccgaa gatgggaaaa agagacatac cctagaaaag    6720
atgactgatt ctgtcacttg tttgtattgc aattcctttt ccaagcaaag caaacaaaaa    6780
aattttcttt tggttggaac cgctgatggc aagttagcaa ttttttgaaga taagactgtt    6840 aagcttaaag gagctgctcc tttgaagata ctaaatatag gaaatgtcag tactccattg    6900
atgtgtttga gtgaatccac aaattcaacg gaaagaaatg taatgtgggg aggatgtggc    6960
acaaagattt tctcctttc taatgatttc accattcaga aactcattga acaagaaca    7020 agccaactgt tttcttatgc agctttcagt gattccaaca tcataacagt ggtggtagac    7080
actgctctct atattgctaa gcaaaatagc cctgttgtgg aagtgtggga taagaaaact    7140
gaaaaactct gtggactaat agactgcgtg cacttttaa gggaggtaat ggtaaaagaa    7200
aacaaggaat caaaacacaa aatgtcttat tctgggagag tgaaaaccct ctgccttcag    7260
aagaacactg ctctttggat aggaactgga ggaggccata ttttactcct ggatctttca    7320
actcgtcgac ttatacgtgt aatttacaac ttttgtaatt cggtcagagt catgatgaca    7380
gcacagctag gaagccttaa aaatgtcatg ctggtattgg gctacaaccg gaaaaatact    7440
gaaggtacac aaaagcagaa agagatacaa tcttgcttga ccgtttggga catcaatctt    7500
ccacatgaag tgcaaaattt agaaaaacac attgaagtga gaaagaatt agctgaaaaa    7560 atgagacgaa catctgttga gtaa                                          7584
```

<210> SEQ ID NO 3
<211> LENGTH: 22
<212> TYPE: DNA
<213> ORGANISM: Artificial Sequence
<220> FEATURE:
<223> OTHER INFORMATION: Primer

<400> SEQUENCE: 3
ttgcagctgt aaggaatttg gg                                            22

<210> SEQ ID NO 4
<211> LENGTH: 21

```
<212> TYPE: DNA
<213> ORGANISM: Artificial Sequence
<220> FEATURE:
<223> OTHER INFORMATION: Primer

<400> SEQUENCE: 4
gcattcttca gcctgagacc c                                              21

<210> SEQ ID NO 5
<211> LENGTH: 22
<212> TYPE: DNA
<213> ORGANISM: Artificial Sequence
<220> FEATURE:
<223> OTHER INFORMATION: Primer

<400> SEQUENCE: 5
tgaaggacac tgaacaagat gg                                             22

<210> SEQ ID NO 6
<211> LENGTH: 22
<212> TYPE: DNA
<213> ORGANISM: Artificial Sequence
<220> FEATURE:
<223> OTHER INFORMATION: Primer

<400> SEQUENCE: 6
gccatagtcc ttccatagtt cc                                             22

<210> SEQ ID NO 7
<211> LENGTH: 18
<212> TYPE: DNA
<213> ORGANISM: Artificial Sequence
<220> FEATURE:
<223> OTHER INFORMATION: Primer

<400> SEQUENCE: 7
cgcagcgagc attgtacc                                                  18

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
ctcggaaagt ttcccaattc                                                20

<210> SEQ ID NO 9
<211> LENGTH: 24
<212> TYPE: DNA
<213> ORGANISM: Artificial Sequence
<220> FEATURE:
<223> OTHER INFORMATION: Primer

<400> SEQUENCE: 9
ctggtattac ctcaactgtg gctc                                           24

<210> SEQ ID NO 10
<211> LENGTH: 23
<212> TYPE: DNA
<213> ORGANISM: Artificial Sequence
<220> FEATURE:
<223> OTHER INFORMATION: Primer

<400> SEQUENCE: 10
actggtatgt ttaagcctgg cac                                            23
```

```
<210> SEQ ID NO 11
<211> LENGTH: 24
<212> TYPE: DNA
<213> ORGANISM: Artificial Sequence
<220> FEATURE:
<223> OTHER INFORMATION: Primer

<400> SEQUENCE: 11
agcagcagag aagatttcaa taac                                    24

<210> SEQ ID NO 12
<211> LENGTH: 22
<212> TYPE: DNA
<213> ORGANISM: Artificial Sequence
<220> FEATURE:
<223> OTHER INFORMATION: Primer

<400> SEQUENCE: 12
aatcatcttt gaaagaacca gg                                      22

<210> SEQ ID NO 13
<211> LENGTH: 24
<212> TYPE: DNA
<213> ORGANISM: Artificial Sequence
<220> FEATURE:
<223> OTHER INFORMATION: Primer

<400> SEQUENCE: 13
taaacgaagc tccctcactg taag                                    24

<210> SEQ ID NO 14
<211> LENGTH: 22
<212> TYPE: DNA
<213> ORGANISM: Artificial Sequence
<220> FEATURE:
<223> OTHER INFORMATION: Primer

<400> SEQUENCE: 14
tctttgtagc tgcggttgtt tc                                      22

<210> SEQ ID NO 15
<211> LENGTH: 24
<212> TYPE: DNA
<213> ORGANISM: Artificial Sequence
<220> FEATURE:
<223> OTHER INFORMATION: Primer

<400> SEQUENCE: 15
tcatgaagat gtctgtgata gggc                                    24

<210> SEQ ID NO 16
<211> LENGTH: 24
<212> TYPE: DNA
<213> ORGANISM: Artificial Sequence
<220> FEATURE:
<223> OTHER INFORMATION: Primer

<400> SEQUENCE: 16
ctctattgtg agcaaactgc atgg                                    24

<210> SEQ ID NO 17
<211> LENGTH: 26
<212> TYPE: PRT
<213> ORGANISM: Homo sapiens

<400> SEQUENCE: 17
```

```
Asp Tyr Gly Ile Ala Gln Tyr Cys Cys Arg Met Gly Ile Lys Thr Ser
1               5                   10                  15

Glu Gly Thr Pro Gly Phe Arg Ala Pro Glu
            20                  25

<210> SEQ ID NO 18
<211> LENGTH: 26
<212> TYPE: PRT
<213> ORGANISM: Homo sapiens

<400> SEQUENCE: 18

Asp Tyr Gly Ile Ser Arg Gln Ser Phe His Glu Gly Ala Leu Gly Val
1               5                   10                  15

Glu Gly Thr Pro Gly Tyr Gln Ala Pro Glu
            20                  25

<210> SEQ ID NO 19
<211> LENGTH: 25
<212> TYPE: PRT
<213> ORGANISM: Homo sapiens

<400> SEQUENCE: 19

Asp Phe Gly Leu Ala Lys Ala Glu Arg Lys Gly Leu Asp Ser Ser Arg
1               5                   10                  15

Leu Pro Val Lys Trp Thr Ala Pro Glu
            20                  25

<210> SEQ ID NO 20
<211> LENGTH: 30
<212> TYPE: PRT
<213> ORGANISM: Homo sapiens

<400> SEQUENCE: 20

Asp Phe Gly Leu Ala Arg Asp Ile Met His Asp Ser Asn Tyr Val Ser
1               5                   10                  15

Lys Gly Ser Thr Phe Leu Pro Val Lys Trp Met Ala Pro Glu
            20                  25                  30

<210> SEQ ID NO 21
<211> LENGTH: 26
<212> TYPE: PRT
<213> ORGANISM: Homo sapiens

<400> SEQUENCE: 21

Asp Phe Gly Leu Ala Arg Glu Trp His Lys Thr Thr Lys Met Ser Ala
1               5                   10                  15

Ala Gly Thr Tyr Ala Trp Met Ala Pro Glu
            20                  25

<210> SEQ ID NO 22
<211> LENGTH: 19
<212> TYPE: PRT
<213> ORGANISM: Homo sapiens

<400> SEQUENCE: 22

Asp Phe Gly Asn Glu Phe Lys Asn Ile Phe Gly Thr Pro Glu Phe Val
1               5                   10                  15

Ala Pro Glu

<210> SEQ ID NO 23
<211> LENGTH: 30
<212> TYPE: PRT
```

```
<213> ORGANISM: Homo sapiens

<400> SEQUENCE: 23

Asp Phe Gly Leu Ala Thr Val Lys Ser Arg Trp Ser Gly Ser His Gln
1               5                   10                  15

Phe Glu Gln Leu Ser Gly Ser Ile Leu Trp Met Ala Pro Glu
            20                  25                  30

<210> SEQ ID NO 24
<211> LENGTH: 17
<212> TYPE: PRT
<213> ORGANISM: Homo sapiens

<400> SEQUENCE: 24

Ile Ala Lys Ile Ala Asp Tyr Gly Ile Ala Gln Tyr Cys Cys Arg Met
1               5                   10                  15

Gly

<210> SEQ ID NO 25
<211> LENGTH: 17
<212> TYPE: PRT
<213> ORGANISM: Tetraodon nigroviridis

<400> SEQUENCE: 25

Ile Ala Lys Ile Thr Asp Tyr Gly Ile Ala Gln His Cys Cys Ser Met
1               5                   10                  15

Gly
```

METHOD OF SCREENING FOR LRRK2-RELATED PARKINSONISM INHERITANCE

This application is a continuation of U.S. Ser. No. 10/568,414, filed Jul. 12, 2006, now U.S. Pat. No. 7,544,786, which is a National Stage application under 35 U.S.C. §371 and claims benefit under 35 U.S.C. §119(a) of International Application No. PCT/NO2005/00465, having an International Filing Date of Dec. 19, 2005, which claims priority from Norwegian Application No. 20052535, filed May 27, 2005, and Norwegian Application No. 20045612, filed on Dec. 23, 2004.

Present invention relates to a novel polynucleotide involved in heritable Parkinson's disease (PD), a novel polypeptide encoded by the polynucleotide, and a method for diagnosing heritable Parkinson's disease (PD).

BACKGROUND

Parkinsonism (MIM168600) is a clinical syndrome characterized by bradykinesia, resting tremor, muscle rigidity, and postural instability (Gelb et al. 1999). The most common cause of parkinsonism is Parkinson's disease (PD). Second to Alzheimer's disease, PD is the most common neurodegenerative disorder affecting >1% of the population over 55 years of age (de Rijk et al. 1995). Neuropathological findings in PD are loss of pigmented neurons in the brainstem, substantia nigra and locus ceruleus, with intracellular Lewy body inclusions found within surviving neurons (Forno 1996).

Although PD is considered a sporadic disease, various hereditary forms of parkinsonism have been recognized (Vila and Przedborski 2004). A major breakthrough in recent years has been the mapping and cloning of a number of genes causing monogenic forms of parkinsonism. Genomic multiplication and missense mutations in the α-synuclein gene were initially identified in a small number of families with autosomal dominant parkinsonism (PARK1/4 [MIM 168601]) (Polymeropoulos et al. 1997; Kruger et al. 1998; Singleton et al. 2003; Chartier-Harlin et al. 2004; Farrer et al. 2004; Zarranz et al. 2004). Subsequently, α-synuclein antibodies were found to robustly stain Lewy bodies and Lewy neurites in the substantia nigra in familial and sporadic PD (Spillantini et al. 1997) and common genetic variability in the α-synuclein promoter has been implicated in sporadic PD (Pals et al. 2004).

Autosomal recessive mutations in three genes, parkin, DJ-1 and PINK1 have been linked with early-onset parkinsonism (<45 years at onset) (PARK2, PARK6 & PARK7 [MIM 602533, 602544 & 608309]) (Kitada et al. 1998; Bonifati et al. 2003; Valente et al. 2004). A large number of pathogenic mutations and rearrangements have been identified in the parkin gene reviewed by (Mata et al. 2004), but mutations in DJ-1 and PINK-1 arc rare (unpublished data).

Very recently, five pathogenic mutations were identified in a gene, leucine-rich repeat kinase 2 (LRRK2) in six families with autosomal-dominant parkinsonism, linked to the PARK8 locus [MIM 607060]) (Zimprich et al. 2004a). Paisan-Ruiz and colleagues independently confirmed these findings of two pathogenic mutations in a British and Basque families (Paisan-Ruiz et al. x2004).

OBJECT

The object of the invention is to isolate a gene or polynucleotide proving inheritable parkinsonism, and to use presence of this gene to diagnose a patient before he/her gets sick. A further object is to use this gene or polynucleotide to transfect a microorganism or experimental animal in order to develop a new medicine for treating or preventing the onset of parkinsonism.

THE INVENTION

Inheritable parkinsonism may be proved by the method according to the characterizing part of claim 5, and the other objects are met by a polynucleotide according to the characterizing part of claim 1, a recombinant vector according to claim 3, a DNA probe and a DNA primer according to claims 4 and 6 respectively, and a peptide according to claim 9.

The inventors have isolated a novel LRRK2 mutation, and this mutation may cause development of dominantly inherited PD. By screening healthy persons, one can state whether the healthy persons have the mutation, and thus most likely will develop the illness.

Using a probe to test whether a patient has the mutation allows a precise, differential diagnosis of this type of Parkinson's disease. The probe represents a safe and accurate biomarker which will be powerful as it nominates subjects, future patients, for neuroprotective therapy. At the present time this is a research enterprise, but not for long. These subjects provide the first (and only) 'uniform substrate/background' for studies on drug efficacy/safety. From a research perspective they will also facilitate models of disease (C. elegans, Drosophila, mice) and epidemiological research on the variable expressivity and age-associated penetrance. As the sequence of the mutated gene is known, microorganisms and further experimental animals may be transfected, in order to investigate for a new medicine to treat or prevent the onset of the illness.

The genetic information provides subjects with the cause of their disease, an explanation for which, if handled correctly, can be of great psychological benefit (fulfilling the 'need to know' why). This information also prioritizes the resources of the research community, grant funding agencies and the pharmaceutical industry on developing a neuroprotective therapies to halt G2019S disease progression.

BRIEF DESCRIPTION OF THE DRAWINGS

In the following the invention will be described by reference to a study of PD patients and their families. Parts of the study are shown in figures, wherein

FIG. 5 shows aligned amino acid sequences of the activation loop of different human kinases: LRRK2 (SEQ ID NO:17), LRRK1 (SEQ ID NO:18), MATK (SEQ ID NO:19), PDGFRA (SEQ ID NO:20), MAP3K10 (SEQ ID NO:21), DAPK1 (SEQ ID NO:22), and BRAF (SEQ ID NO:23).

DETAILED DESCRIPTION

Figure 1:
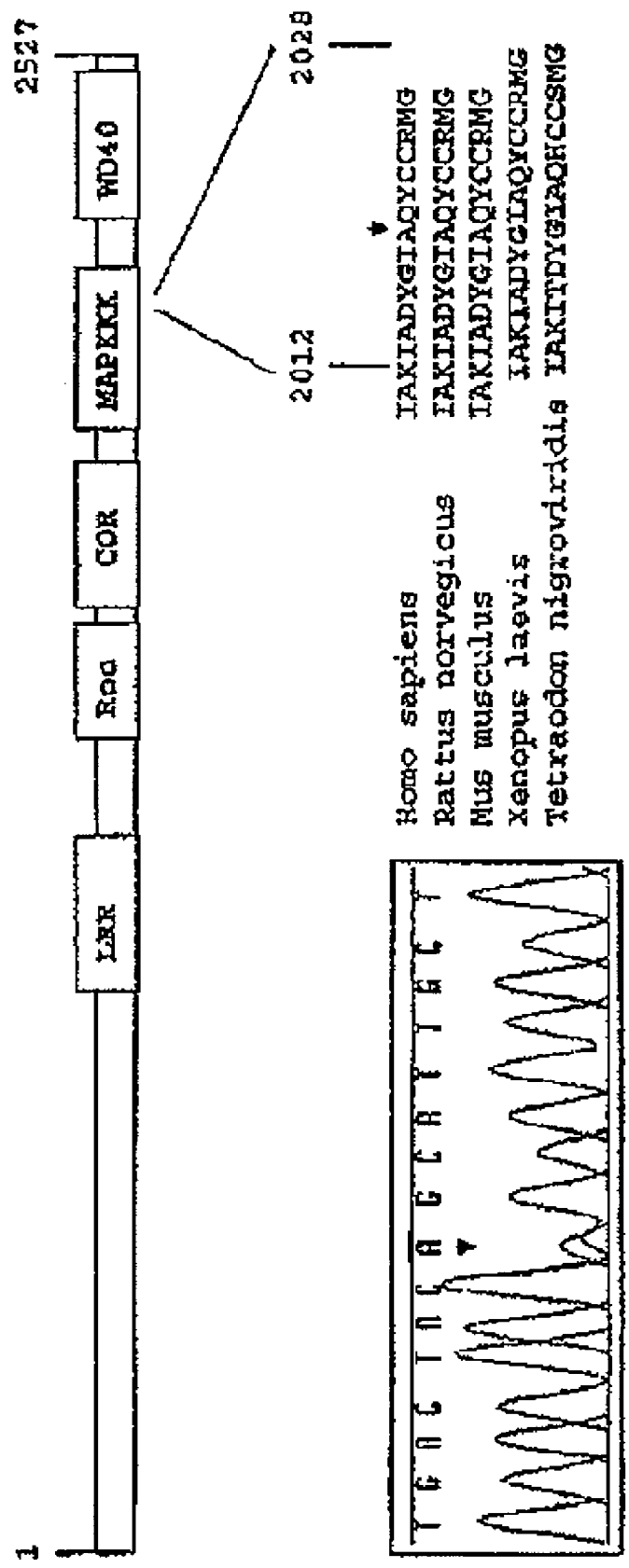
FIG. 1 shows a schematic drawing of LRRK2 with predicted protein domains. The LRRK2 protein sequence in the region of the G2019S mutation is aligned for orthologs from human, rat, mouse, and frog (all SEQ ID NO:24), as well as puffer fish (SEQ ID NO:25).

The inventors identified seven unrelated persons all having the new mutation, from 248 multiplex kindreds with dominantly inherited PD, and six further unrelated persons from three population-based series of persons with dominantly inherited PD. These 13 persons and their families made basis for the inventors' further work. Segregation and linkage analysis provides evidence for pathogenicity and an estimate of age-associated penetrance; haplotype analysis demonstrates the mutation originates from a common and ancient founder.

Subjects and Methods

Study Subjects

The patients and controls were examined by neurologists specialized in movement disorders. A full history, including family history and neurological examination, was completed on each patient. Clinical diagnosis of PD required the presence of at least two of three cardinal signs (resting tremor, bradykinesia and rigidity), improvement from adequate dopaminergic therapy and the absence of atypical features or other causes of parkinsonism.

LRRK2 Sequencing and Mutation Screening

Blood samples were taken and genomic DNA was extracted using standard techniques. Six families (families 194, 281, 3081, 3082, 3083 and 3211) were known to have a positive LOD-score for STR (Short Tandem Repeat) markers in the PARK8 locus (Zimprich et al. 2004b). Amplification of all 51 exons of the LRRK2 gene was performed by polymerase chain reaction (PCR) in one patient having PD, from each of these six families. All PCRs were carried out for each primer set with 20-50 ng of template DNA in a total volume of 25 .mu.l using a final reaction concentration of 200 µM dNTP, 1×PCR-Buffer (Qiagen), 1× Q-Solution (Qiagen), and 0.8 µM of each primer. One unit of Taq polymerase (Qiagen) was added to each reaction. Amplification was performed using a 57-52 C.°-touchdown protocol over 38 cycles. The primers used for PCR amplification of LRRK2 exons and for sequencing are available on request.

The nucleotide sequences of all PCR products were determined by direct sequencing. Each PCR product was cleaned by using a Millipore PCR purification plate. Three microliters of purified PCR product was used per sequencing reaction with 1 µl of either the forward or reverse PCR primer and 1 µl of BigDye reaction mix (Applied Biosystems). Electrophoresis was performed under standard conditions on an ABI 3730 automated sequencer (Applied Biosystems). All sequences were obtained with both forward and reverse primers. Sequences were analyzed with SeqScape software version 2.1.1 (Applied Biosystems) and compared with published sequence of LRRK2 (GenBank accession no. AY792511).

After identification of a heterozygous G2019S (G6055A) mutation in the proband of family 3215 (referred to as family 3211 in Zimprich et al, 2004b), we designed a probe employing TaqMan chemistry on an ABI7900 (Applied Biosystems) to screen for this mutation. First we examined 248 PD patients from families with a known family history, consistent with autosomal dominant transmission of a suspected causative gene. Then 377 Norwegian, 271 Irish and 100 Polish PD patients (constituting the three population series) were checked using this assay; and 2260 samples of healthy persons from similar populations were also included (1200 US American, 550 Norwegian, 330 Irish and 180 Polish subjects), the latter to be used as control samples. Mutations were confirmed by direct sequencing of PCR products from LRRK2 exon 41. Finally, all participating family members of LRRK2 G2019 mutation carriers (affected and unaffected) were screened for the mutation.

By 6055 G>A or G6055A it is meant that nucleotide number 6055 of the LRRK2 gene, counted from the 5'end of the polynucleotide, has changed from G (guanine) to A (adenine). This change also causes a change in the polypeptide encoded by the polynucleotide, and G2019S denotes a polynucleotide where amino acid number 2019 is changed from G (Glycine) to S (Serine). These shortenings are well known to persons skilled of the art.

Genotyping of STR Markers

Fourteen STR markers were genotyped in mutation carriers and all available family members, in all 13 families, for linkage analyses and to determine whether there was a particular haplotype associated with the LRRK2 mutation. STR markers were chosen to span the PARK8 region including D12S87, D12S1648, D12S2080, D12S2194, D12S1048, D12S1301 and D12S1701. LRRK2 is located between D12S2194 and D12S1048. We also developed seven novel STR markers in this region (shown in table 1 below) by searching for repeat polymorphisms using RepeatMasker of in silico BAC sequence (UCSC Human Genome Browser Web site). The labeling of these novel markers reflects their physical position relative to the start codon of LRRK2.

TABLE 1

Novel chromosome 12 STR markers

| Marker name | Primer sequence | Physical position (bp) On chromosome 12 | SEQ ID NO: |
|---|---|---|---|
| D12S2514 | F: 5'-TTGCAGCTGTAAGGAATTTGGG-3' | 38873779 | 3 |
|  | R: 5'-GCATTCTTCAGCCTGAGACCC-3' |  | 4 |
| D12S2515 | F: 5'-TGAAGGACACTGAACAAGATGG-3' | 38974140 | 5 |
|  | R: 5'-GCCATAGTCCTTCCATAGTTCC-3' |  | 6 |
| D12S2516 | F: 5'-CGCAGCGAGCATTGTACC-3' | 38989214 | 7 |
|  | R: 5'-CTCGGAAAGTTTCCCAATTC-3' |  | 8 |
| D12S2518 | F: 5'-CTGGTATTACCTCAACTGTGGCTC-3' | 39034800 | 9 |
|  | R: 5'-ACTGGTATGTTTAAGCCTGGCAC-3' |  | 10 |
| D12S2519 | F: 5'-AGCAGCAGAGAAGATTTCAATAAC-3' | 39116816 | 11 |
|  | R: 5'-AATCATCTTTGAAAGAACCAGG-3' |  | 12 |

TABLE 1-continued

Novel chromosome 12 STR markers

| Marker name | Primer sequence | Physical position (bp) On chromosome 12 | SEQ ID NO: |
|---|---|---|---|
| D12S2523 | F: 5'-TAAACGAAGCTCCCTCACTGTAAG-3' | 39147728 | 13 |
|  | R: 5'-TCTTTGTAGCTGCGGTTGTTTC-3' |  | 14 |
| D12S2517 | F: 5'-TCATGAAGATGTCTGTGATAGGGC-3' | 39282976 | 15 |
|  | R: 5'-CTCTATTGTGAGCAAACTGCATGG-3' |  | 16 |

One primer of each pair was labeled with a fluorescent tag. PCR reactions were carried out on 10-20 ng of DNA in a total volume of 15 μl with final reaction concentrations of 150 μM dNTP, 1×PCR-Buffer (Qiagen), 1× Q-Solution (Qiagen) and 0.6 μM of each primer, with 1 unit of Taq Polymerase (Qiagen). Amplification was performed using a 57-52° C.-touchdown protocol over 38 cycles. The PCR product for each marker was diluted by a factor of 10 to 100 with water. One microliter was then added to 10 .mu.l of Hi-Di Formamide and Rox size standard. All samples were run on an ABI 3100 genetic analyzer, and results were analyzed using Genescan 3.7 and Genotyper 3.7 software (Applied Biosystems). Since population allele frequencies were not available from the CEPH database, these have been estimated by genotyping 95 unrelated Caucasian subjects, a population based series from the United States (shown in table 2 below).

TABLE 2

Allele frequencies of Park 8 Markers

| Marker and allele (bp) | Frequency (%) |
|---|---|
| D12S87 (n = 92) |  |
| 150 | 0.5 |
| 154 | 1.1 |
| 156 | 27.2 |
| 158 | 33.2 |
| 160 | 11.4 |
| 162 | 2.7 |
| 164 | 6.0 |
| 166 | 17.4 |
| 168 | 0.5 |
| D12S1648 (n = 91) |  |
| 110 | 13.7 |
| 112 | 3.3 |
| 114 | 11.0 |
| 116 | 4.4 |
| 118 | 2.2 |
| 120 | 2.8 |
| 122 | 17.0 |
| 124 | 3.9 |
| 126 | 7.7 |
| 128 | 14.3 |
| 130 | 8.8 |
| 132 | 2.8 |
| 134 | 2.8 |
| 136 | 1.7 |
| 138 | 0.6 |
| 140 | 2.2 |
| 142 | 1.1 |
| D12S2080 (n = 93) |  |
| 176 | 1.6 |
| 180 | 20.2 |
| 184 | 44.7 |
| 188 | 22.9 |
| 192 | 10.6 |
| D12S2194 (n = 87) |  |
| 245 | 0.6 |
| 249 | 40.9 |
| 253 | 32.4 |
| 257 | 19.9 |
| 261 | 4.6 |
| 265 | 1.7 |
| D12S2514 (n = 82) |  |
| 284 | 11.0 |
| 291 | 53.1 |
| 294 | 32.3 |
| 297 | 1.2 |
| 300 | 2.4 |
| D12S2515 (n = 93) |  |
| 208 | 3.2 |
| 212 | 26.6 |
| 216 | 18.6 |
| 220 | 22.9 |
| 224 | 20.7 |
| 228 | 5.3 |
| 232 | 2.7 |
| rs 7966550 (n = 90) |  |
| T | 90.6 |
| C | 9.4 |
| DS12S2516 |  |
| 252 | 37.3 |
| 254 | 62.7 |
| rs 1427263 (n = 89) |  |
| A | 63.6 |
| C | 36.5 |
| rs1116013 (n = 88) |  |
| A | 49.4 |
| G | 50.6 |
| rs11564148 (n = 88) |  |
| A | 26.1 |
| T | 73.9 |
| D12S2518 (N = 90) |  |
| 154 | 79.7 |
| 168 | 15.9 |
| 170 | 4.4 |
| D12S519 (n = 72) |  |
| 132 | 29.5 |
| 134 | 22.6 |
| 138 | 22.6 |

TABLE 2-continued

Allele frequencies of Park 8 Markers

| Marker and allele (bp) | Frequency (%) |
|---|---|
| 140 | 25.3 |
| D12S2520 (N = 85) | |
| 248 | 8.2 |
| 251 | 7.6 |
| 254 | 10.0 |
| 257 | 54.1 |
| 260 | 20.0 |
| D12S2521 (N = 93) | |
| 311 | 0.5 |
| 315 | 10.8 |
| 319 | 20.4 |
| 323 | 8.1 |
| 327 | 7.0 |
| 331 | 8.1 |
| 335 | 0.5 |
| 355 | 1.1 |
| 359 | 7.5 |
| 363 | 13.4 |
| 367 | 7.0 |
| 371 | 7.0 |
| 375 | 6.5 |
| 379 | 3.8 |
| 383 | 1.1 |
| 387 | .5 |
| D12S2522 (N = 93) | |
| 281 | 9.1 |
| 283 | 14.0 |
| 285 | .5 |
| 287 | 11.3 |
| 293 | .5 |
| 295 | 15.6 |
| 297 | 44.6 |
| 299 | 4.3 |
| D12S2523 (n = 89) | |
| 305 | 18.9 |
| 314 | 41.1 |
| 317 | 8.9 |
| 320 | 30.0 |
| 323 | 1.1 |
| 180 | 8.5 |
| 182 | 7.5 |
| 184 | 15.4 |
| 186 | 8.5 |
| 188 | 11.7 |
| 190 | 8.0 |
| 192 | 5.3 |
| 194 | 1.1 |
| 196 | 1.1 |
| 198 | 3.2 |
| 200 | 0.5 |
| 202 | 3.7 |
| 204 | 6.9 |
| 206 | 6.9 |
| 208 | 4.3 |
| 210 | 2.1 |
| 212 | 3.2 |
| 214 | 1.6 |
| 216 | 0.5 |
| D12S1048 (n = 89) | |
| 211 | 37.2 |
| 214 | 21.1 |
| 217 | 17.8 |
| 220 | 2.2 |
| 223 | 6.7 |
| 226 | 11.7 |
| 229 | 3.3 |
| D12S1301 (n = 93) | |
| 96 | 0.5 |
| 100 | 37.2 |
| 104 | 17.6 |
| 108 | 11.1 |
| 112 | 12.2 |
| 116 | 13.3 |
| 120 | 7.5 |
| 124 | 0.5 |
| D12S1701 (n = 93) | |
| 89 | 4.3 |
| 91 | 4.8 |
| 93 | 10.8 |
| 95 | 40.0 |
| 97 | 16.0 |
| 99 | 12.4 |
| 101 | 11.8 |
| 103 | 0.5 |

A The number of individuals genotyped is given for each marker (n)
B Alle frequencies are for individual markers in U.S. control subjects Statistical Analysis Multipoint nonparametric LOD scores for all families were calculated using GENEHUNTER-PLUS (Kong and Cox 1997). The frequency of the deleterious allele was set at 0.0001, and empirically determined allele frequencies were employed. The map positions for each marker were taken from Rutgers combined linkage-physical map version 1.0 (MAP-O-MAT web site). The three loci D12S2080, D12S2194 and D12S1301 are very tightly linked, with no observed recombinants in the database or within our genotyped families, and thus inter-marker distances were assigned as 0.01 cM.

Chromosome 12 haplotypes in the PARK8 region were established for those families in which chromosome phase for mutation-carrying individuals could be deduced, thereby determining which alleles co-segregated with the LRRK2 G2019S mutation in each family. For those affected individuals in whom the associated allele for a marker could not be determined, both alleles are given.

The age-dependent penetrance was estimated as the probability of a gene carrier becoming affected, at a given age, within the 13 families. The number of affected mutation carriers, for each decade, was divided by the total number of affected individuals, plus the number of unaffected carriers within that range. For some affected family members no DNA was available and only historical data on the disease course was obtained. These individuals were excluded from penetrance calculations.

Results

Figure 2:
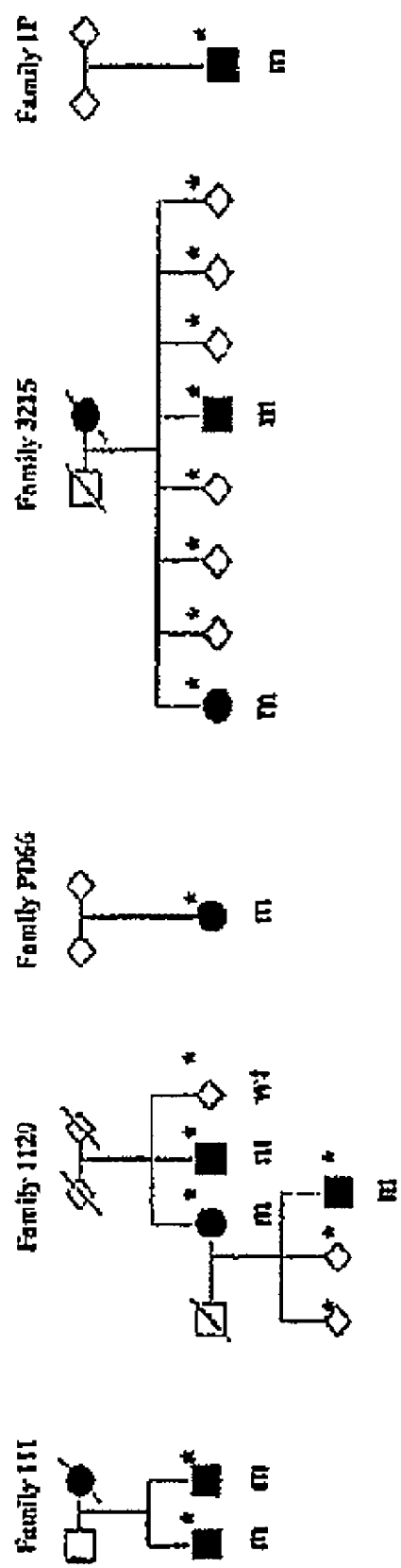
FIG. 2 shows pedigrees of families with LRRK2 G2019S.

As mentioned previously, we identified 13 affected probands (i.e. 13 patients) who carry a heterozygous G6055A mutation in exon 41 of the LRRK2 gene. The mutation leads to a G2019S amino acid substitution of a highly conserved residue within the predicted activation loop of the MAPKKK (Mitogen-Activated Protein Kinase Kinase Kinase) domain (FIG. 1). After genotyping a total of 42 additional family members, 22 additional subjects were found to carry the mutation, seven with a diagnosis of PD (shown in table 3 below). One affected member of family P-089 did not carry the mutation and, for the purposes of this study, was considered a phenocopy and excluded from further analyses. Seven families originated from Norway, three were from the United States, two from Ireland, and one was from Poland. One family from the United States descended from Russian/Rumania, and another from Italy. For only one family (family 111), the ethnic origin was unknown. The LRRK2 G2019S mutation segregates with disease in all kindreds, consistent with autosomal dominant transmission. To ensure patient confidentiality, simplified versions of the family pedigrees are presented in FIG. 2. There was no evidence of the mutation in the 2260 control samples.

Figure 4:
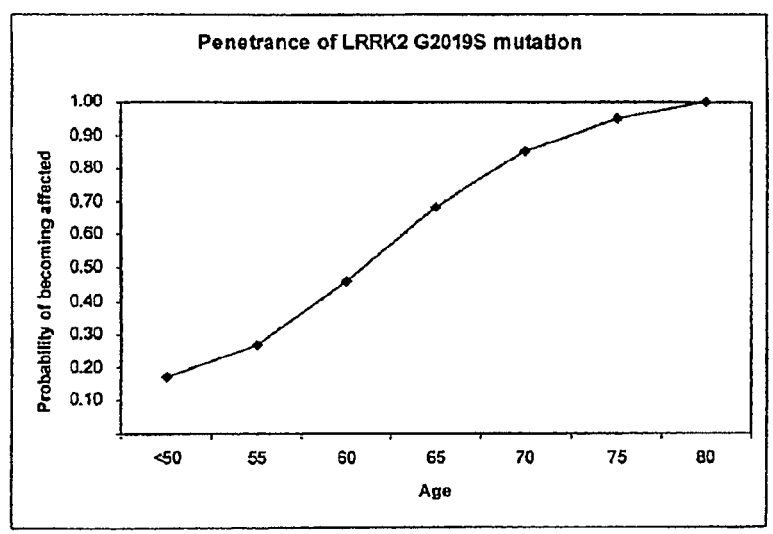
FIG. 4 shows probability of becoming affected by parkinsonism, in LRRK2 G2019S carriers, as a function of age.

Age at onset of clinical symptoms was quite variable, even within the same family. Family 1120, a family from the United States, had both the earliest and latest age at onset for a patient. The youngest affected subject had an onset at 39 years, whereas the oldest carrier presented with initial symptoms at 78 years. Where recorded, most LRRK2 G2019S carriers have late-onset disease (>50 years at onset). The mean age at onset of affected mutation carriers was 56.8 years (range 39-78 years, n=19). Unaffected carriers have a mean age of 53.9 years (range 26-74 years, n=14). The penetrance of the mutation was found to be highly age-dependent, increasing from 17% at the age of 50 to 85% at the age of 70 (FIG. 4).

Discussion

We have identified a novel LRRK2 mutation, G2019S, which co-segregates with autosomal dominant parkinsonism in 13 kindreds originating from several European populations. Positive LOD scores were obtained in multiplex families, and combined they provide significant support for the PARK8 locus. LRRK2 G2019S mutation was absent in a large number of control subjects, and of similar ethnicity. The number of families linked to LRRK2 in this and previous studies now explains the majority of genetically defined autosomal dominant parkinsonism.

The mean age at onset of affected LRRK2 G2019S carriers was 56.8 years, and comparable to that of patients in other families linked to PARK8 (Funayama et al. 2002; Paisan-Ruiz et al. 2004; Zimprich et al. 2004a). The majority of patients present with late-onset disease, indistinguishable from typical idiopathic PD. Disease penetrance is age-dependent, and increases in a linear fashion from 17% at the age of

TABLE 3

Demographic and Clinical Information for 13 Families with LRRK2 G2019S

| CHARACTERISTIC | FINDINGS FOR FAMILY | | | | | | | | | | | | |
|---|---|---|---|---|---|---|---|---|---|---|---|---|---|
| | P-063 | P-089 | P-104 | P-241 | P-369 | P-394 | F05 | 1210 | 111 | 1120 | PD66 | 3211 | IP |
| Country of origin | Norway | Norway | Norway | Norway | Norway | Norway | Norway | United States | United States | United States | Ireland | Ireland | Poland |
| No. of generations | 3 | 4 | 3 | 3 | 3 | 4 | 4 | 2 | 2 | 3 | 1 | 2 | 1 |
| No. of affected individuals | 2 | 4 | 4 | 1 | 3 | 4 | 5 | 2 | 3 | 3 | 1 | 3 | 1 |
| No. of typed individuals affected (unaffected) | 1 (6) | 2 (8) | 1 (1) | 1 (4) | 2 (3) | 1 (1) | 3 (6) | 1 (0) | 2 (0) | 3 (3) | 1 (0) | 2 (6) | 1 (0) |
| No. of typed generations | 2 | 3 | 1 | 2 | 1 | 2 | 2 | 1 | 1 | 2 | 1 | 1 | 1 |
| Age[3] at onset in years (range) | 59 (53-65) | 59 (43-70) | 58 | 60 (43-61) | 50 | 66 (61-70) | 64 | 65 (57-58) | 58 (39-78) | 59 | 41 (40-52) | 46 | 73 |
| Maximum mLOD score | 0 | .30 | 0 | 0 | .60 | 0 | .90 | 0 | .09 | .30 | 0 | .30 | 0 |

[3]Average ages at onset are given when affected individuals. n ≥ 2

Evidence for linkage (the statistical burden of proof that this mutation causes disease) to the PARK8 locus was found across families, with a combined maximum multipoint LOD score of 2.41 [for all 14 markers], corresponding to a P value of $4.3 \times 10^{-4}$ As only a defined chromosomal region was investigated, rather than a genome-wide search, this LOD score exceeds that required for significance, P=0.01 (Lander and Kruglyak 1995). A positive LOD score was found in all families where more then one affected subject was genotyped (table 3).

Figure 3:
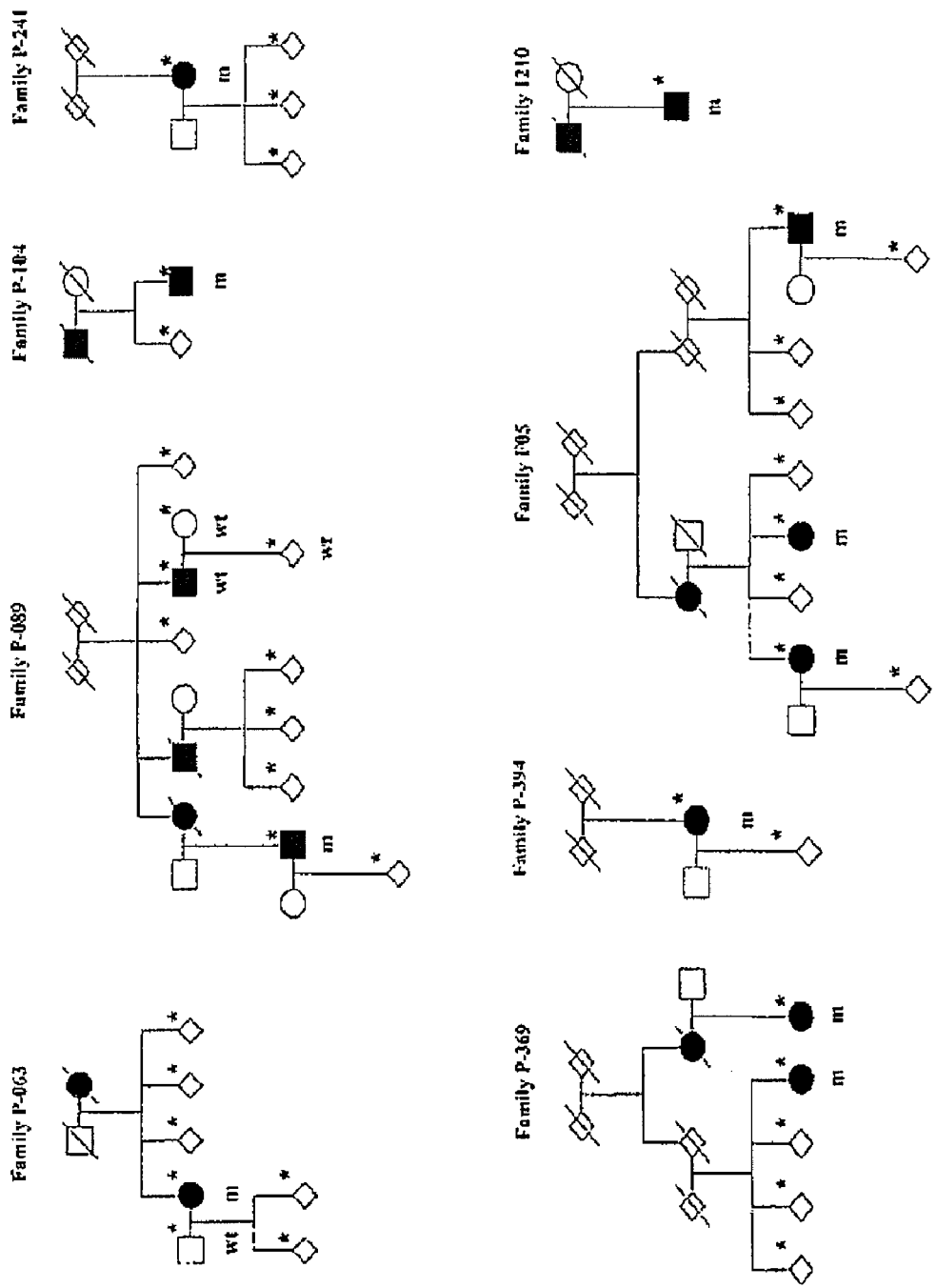
FIG. 3 shows chromosome 12q12 STR markers on the disease haplotype (PARK 8)

All affected members from the different families, except the individual in family P-089 who did not carry the mutation, appear to share a common haplotype on chromosome 12 the LRRK2 gene locus (FIG. 3). Haplotypes can be established with certainty in nine of the families, and all mutation carriers in these families share alleles for four STR markers and 4 single nucleotide polymorphisms (SNPs) in the LRRK2 gene locus. These markers are LRRK2 D12S2516, D12S2518, D12S2519, D12S2520 and SNPs rs7966550, rs1427263, rs11176013, rs11564148. For the remaining families, the number of available samples from relatives was not sufficient to determine phase. However, the genotypes in these cases are consistent with a common LRRK2 G2019S allele. D12S2516 is located in intron 29 and D12S2518 is located in intron 44 of the LRRK2 gene, whereas the two other shared markers are positioned 3' of the gene. Using the physical position of the shared and non-shared markers, the size of the shared haplotype is between 145 kb and 154 kb.

50 to 85% at the age of 70. Age is the single most consistent risk factor for development of PD and other neurodegenerative disorders (Lang and Lozano 1998), and an important risk factor in LRRK2 associated parkinsonism. Interestingly, age at onset was variable in this study, both within and between different families, suggesting other susceptibility factors, environmental or genetic, may influence the phenotype.

Although our findings clearly indicate that LRRK2 mutations account for a substantial proportion of familial late-onset parkinsonism, historically, cross-sectional twin studies have not supported a genetic etiology for late-onset PD (Tanner et al. 1999; Wirdefeldt et al. 2004). The age-associated penetrance of LRRK2 mutations provides some explanation as even large and well designed twin studies are underpowered to detect incompletely penetrant mutations (Simon et al. 2002). LRRK2 mutations were also found in apparently sporadic PD patients; three of the patients in this study did not have any known affected first- or second-degree relatives. However, a caveat of age-dependent penetrance is that carriers may die of other diseases, before manifesting or being diagnosed with PD. Thus, it seems difficult to separate sporadic and familial PD, or to hypothesize environmental causes to be more important in one group and genetic causes more prominent in the other. In light of these results, a family history of parkinsonism, previously considered an exclusion criterion for a diagnosis of PD, must be reconsidered (Hughes et al. 1992).

LRRK2 is a member of the recently defined ROCO protein family (Bosgraaf and Van Haastert 2003). In human, mouse and rat, members of the ROCO protein family have five conserved domains (FIG. 1). The kinase domain belongs to the MAPKKK subfamily of kinases. The active sites of all kinases are located in a cleft between an N-terminal and a C-terminal lobe, typically covered by an 'activation loop', in an inactive conformation. The activation loop must undergo crucial structural changes to allow access to peptide substrates and to orientate key catalytic amino acids (Huse and Kuriyan 2002). In different kinases, the activation loop starts and ends with the conserved residues asp-phe-gly (DFG) and ala-pro-glu (APE), respectively (Dibb et al. 2004). Of note, the LRRK2 G2019S substitution changes a highly conserved amino acid at the start of this loop (FIG. 5). In a German family we previously described, an 12020T mutation is located in an adjacent codon (Zimprich et al. 2004a). In other kinases, oncogenic mutations in residues within the activation loop of the kinase domain have an activating effect (Davies et al. 2002), thus we postulate LRRK2 G2019S and 12020T mutations may have an effect on its kinase activity.

The age of an allele may be estimated from the genetic variation among different copies (intra-allelic variation), or from its frequency (Slatkin and Rannala 2000). However, the local recombination rate on chromosome 12q12 is unknown, as is the frequency of the G2019S mutation in the general population. Nevertheless, at centromeres there is generally a dearth in recombination; indeed no crossovers have been observed between LRRK2 flanking markers D12S2194 and D12S1048 in our studies, or within CEPH families (MAP-O-MAT web site). The physical size of the shared haplotype is also small, between 145 kb and 154 kb, and the allele is widespread in families from several European populations. Hence, the mutation is likely to be ancient and may be relatively common in specific populations. These data suggest a substantial proportion of late-onset PD will have a genetic basis.

Electronic-Database Information

The physical position of markers is from NCBI build 34. Accession numbers and URLs for data presented herein are as follows:

Online Mendelian Inheritance in Man (OMIM), World Wide Web at ncbi.nlm.nih.gov/Omim/MAP-O-MAT, compgen.rutgers.edu/mapomat RepeatMasker, World Wide Web at repeatmasker.org/

REFERENCES

Bonifati V, Rizzu P, van Baren M J, Schaap O, Breedveld G J, Krieger E, Dekker M C, Squitieri F, Ibanez P, Joosse M, van Dongen J W, Vanacore N, van Swieten J C, Brice A, Meco G, van Duijn C M, Oostra B A, Heutink P (2003) Mutations in the DJ-1 gene associated with autosomal recessive early-onset parkinsonism. Science 299:256-9

Bosgraaf L, Van Haastert P J (2003) Roc, a Ras/GTPase domain in complex proteins. Biochim Biophys Acta 1643:5-10

Chartier-Harlin M C, Kachergus J, Roumier C, Mouroux V, Douay X, Lincoln S, Levecque C, Larvor L, Andrieux J, Hulihan M, Waucquier N, Defebvre L, Amouyel P, Farrer M, Destee A (2004) Alpha-synuclein locus duplication as a cause of familial Parkinson's disease. Lancet 364:1167-9

Davies H, Bignell G R, Cox C, Stephens P, Edkins S, Clegg S, Teague J, et al. (2002) Mutations of the BRAF gene in human cancer. Nature 417:949-54 de Rijk M C, Breteler M M, Graveland G A, Ott A, Grobbee D E, van der Meche F G, Hofman A (1995) Prevalence of Parkinson's disease in the elderly: the Rotterdam Study. Neurology 45:2143-6

Dibb N J, Dilworth S M, Mol C D (2004) Switching on kinases: oncogenic activation of BRAF and the PDGFR family. Nat Rev Cancer 4:718-27

Farrer M, Kachergus J, Forno L, Lincoln S, Wang D S, Hulihan M, Maraganore D, Gwinn-Hardy K, Wszolek Z, Dickson D, Langston J W (2004) Comparison of kindreds with parkinsonism and alpha-synuclein genomic multiplications. Ann Neurol 55:174-9

Forno L S (1996) Neuropathology of Parkinson's disease. J Neuropathol Exp Neurol Funayama M, Hasegawa K, Kowa H, Saito M, Tsuji S, Obata F (2002) A new locus for Parkinson's disease (PARK8) maps to chromosome 12p11.2-q13.1. Ann Neurol 51:296-301

Gelb D J, Oliver E, Gilman S (1999) Diagnostic criteria for Parkinson disease. Arch Neurol 56:33-9

Hughes A J, Daniel S E, Kilford L, Lees A J (1992) Accuracy of clinical diagnosis of idiopathic Parkinson's disease: a clinico-pathological study of 100 cases. J Neurol Neurosurg Psychiatry 55:181-4

Huse M, Kuriyan J (2002) The conformational plasticity of protein kinases. Cell 109:275-82

Kitada T, Asakawa S, Hattori N, Matsumine H, Yamamura Y, Minoshima S, Yokochi M, Mizuno Y, Shimizu N (1998) Mutations in the parkin gene cause autosomal recessive juvenile parkinsonism. Nature 392:605-8

Kong A, Cox N J (1997) Allele-sharing models: LOD scores and accurate linkage tests. Am J Hum Genet 61:1179-88

Kruger R, Kuhn W, Muller T, Woitalla D, Graeber M, Kosel S, Przuntek H, Epplen J T, Schols L, Riess O (1998) Ala30Pro mutation in the gene encoding alpha-synuclein in Parkinson's disease. Nat Genet 18:106-8

Lander E, Kruglyak L (1995) Genetic dissection of complex traits: guidelines for interpreting and reporting linkage results. Nat Genet 1:241-7

Lang A E, Lozano A M (1998) Parkinson's disease. First of two parts. N Engl J Med Mata I F. Lockhart P J, Farrer M J (2004) Parkin genetics: one model for Parkinson's disease. Hum Mol Genet 13 Spec No 1:R127-33

Paisan-Ruiz C, Jain S, Evans E W, Gilks W P, Simon J, van der Brug M, de Munain A L, Aparicio S, Gil A M, Khan N, Johnson J, Martinez J R, Nicholl D, Carrera I M, Pena A S, de Silva R, Lees A, Marti-Masso J F, Perez-Tur J, Wood N W, Singleton A B (2004) Cloning of the Gene Containing Mutations that Cause PARK8-Linked Parkinson's Disease. Neuron 44:595-600

Pals P, Lincoln S, Manning J, Heckman M, Skipper L, Hulihan M, Van den Broeck M, De Pooter T, Cras P, Crook J, Van Broeckhoven C, Farrer M J (2004) alpha-Synuclein promoter confers susceptibility to Parkinson's disease. Ann Neurol 56:591-5

Polymeropoulos M H, Lavedan C, Leroy E, Ide S E, Dehejia A, Dutra A, Pike B, Root H, Rubenstein J, Boyer R, Stenroos E S, Chandrasekharappa S, Athanassiadou A, Papapetropoulos T, Johnson W G, Lazzarini A M, Duvoisin R C, Di Torio G, Golbe L I, Nussbaum R L (1997) Mutation in the alpha-synuclein gene identified in families with Parkinson's disease. Science Simon D K, Lin M T, Pascual-Leone A (2002) "Nature versus nurture" and incompletely penetrant mutations. J Neurol Neurosurg Psychiatry 72:686-9

Singleton A B, Farrer M, Johnson J, Singleton A, Hague S, Kachergus J, Hulihan M, Peuralinna T, Dutra A, Nussbaum R, Lincoln S, Crawley A, Hanson M, Maraganore D, Adler C, Cookson M R, Muenter M, Baptista M, Miller D, Blancato J, Hardy J, Gwinn-Hardy K (2003) alpha-Synuclein locus triplication causes Parkinson's disease. Science 302: 841

Slatkin M, Rannala B (2000) Estimating allele age. Annu Rev Genomics Hum Genet 1:225-49

Spillantini M G, Schmidt M L, Lee V M, Trojanowski J Q, Jakes R, Goedert M (1997) Alpha-synuclein in Lewy bodies. Nature 388:839-40

Tanner C M, Ottman R, Goldman S M, Ellenberg J, Chan P, Mayeux R, Langston J W (1999) Parkinson disease in twins: an etiologic study. Jama 281:341-6

Valente E M, Abou-Sleiman P M, Caputo V, Muqit M M, Harvey K, Gispert S, Ali Z, Del Turco D, Bentivoglio A R, Healy D G, Albanese A, Nussbaum R, Gonzalez-Maldonado R, Deller T, Salvi S, Cortelli P, Gilks W P, Latchman D S, Harvey R J, Dallapiccola B, Auburger G. Wood N W (2004) Hereditary early-onset Parkinson's disease caused by mutations in PINK1. Science 304:1158-60

Vila M, Przedborski S (2004) Genetic clues to the pathogenesis of Parkinson's disease. Nat Med 10 Suppl:S58-62

Wirdefeldt K, Gatz M, Schalling M, Pedersen N L (2004) No evidence for heritability of Parkinson disease in Swedish twins. Neurology 63:305-11

Zarranz J J, Alegre J, Gomez-Esteban J C, Lezcano E, Ros R, Ampuero I, Vidal L, Hoenicka J, Rodriguez O, Atares B, Llorens V, Gomez Tortosa E, del Ser T, Munoz D G, de Yehenes J G (2004) The new mutation, E46K, of alpha-synuclein causes Parkinson and Lewy body dementia. Ann Neurol 55:164-73

Zimprich A, Biskup S, Leitner P, Lichtner P, Farrer M, Lincoln S, Kachergus J, Hulihan M, Uitti R J, Caine D B, Stoessl A J, Pfeiffer R F, Patenge N, Carbajal I C, Vieregge P, Asmus F, Muller-Myhsok B, Dickson D W, Meitinger T, Strom T M, Wszolek Z K, Gasser T (2004a) Mutations in LRRK2 Cause Autosomal-Dominant Parkinsonism with Pleomorphic Pathology. Neuron 44:601-7

Zimprich A, Muller-Myhsok B, Farrer M, Leitner P, Shanna M, Hulihan M, Lockhart P, Strongosky A, Kachergus J, Calne D B, Stoessl J, Uitti R J, Pfeiffer R F, Trenkwalder C, Homann N, Ott E, Wenzel K, Asmus F, Hardy J, Wszolek Z, Gasser T (2004b) The PARK8 locus in autosomal dominant parkinsonism: confirmation of linkage and further delineation of the disease-containing interval. Am J Hum Genet 74:11-9

The invention claimed is:

1. A method for classifying a human subject as having or not having LRRK2-related Parkinsonism inheritance, comprising
determining whether the human subject to be screened for Parkinsonism inheritance comprises a LRRK2 polynucleotide having a G or an A at the position corresponding to position 6055 of SEQ ID NO:2, wherein said determining comprises amplifying DNA from said subject and sequencing said amplified DNA to determine whether a G or an A is present at the position corresponding to position 6055 of SEQ ID NO:2, and
classifying said subject as having LRRK2-related Parkinsonism inheritance if said subject comprises an A at the position corresponding to position 6055 of SEQ ID NO:2, or classifying said subject as not having LRRK2-related Parkinsonism inheritance if said subject comprises a G at the position corresponding to position 6055 of SEQ ID NO:2.

2. The method of claim 1, wherein said DNA amplified from said subject is from the blood of said subject.

3. A method for classifying a human subject as having or not having LRRK2-related Parkinsonism inheritance, comprising:
(a) contacting DNA amplified from the human subject with a DNA probe specific for a polynucleotide having the sequence of SEQ ID NO:2 or the complement of SEQ ID NO:2, wherein said probe contains more than ten consecutive nucleotides from SEQ ID NO:2 or from the complement thereof, wherein said probe contains nucleotide position 6055 of SEQ ID NO:2 or the corresponding position of the complement of SEQ ID NO:2, and wherein the ability of said probe to hybridize to said amplified DNA indicates whether said subject has an A or a G at position 6055 of SEQ ID NO:2 or a T or a C at the position corresponding to the complement of position 6055 of SEQ ID NO:2; and
(b) based on said hybridization, classifying said human subject as having LRRK2-related Parkinsonism inheritance if said DNA amplified from said subject has an A at position 6055 of SEQ ID NO:2 or a T at the position corresponding to the complement of position 6055 of SEQ ID NO:2, and classifying said human subject as not having LRRK2-related Parkinsonism inheritance if said DNA amplified from said subject has a G at position 6055 of SEQ ID NO:2 or a C at the position corresponding to the complement of position 6055 of SEQ ID NO:2.

4. The method of claim 3, wherein said DNA is obtained by amplification of DNA from the subject's blood.

5. A method for determining whether a human subject has Parkinsonism inheritance, comprising providing a DNA sample from said subject, and assaying said sample to determine whether said sample comprises a polynucleotide corresponding to SEQ ID NO:2, with the proviso that said polynucleotide comprises an A at the position corresponding to position 6055 of SEQ ID ON:2, wherein the presence of an A at the position corresponding to position 6055 of SEQ ID NO:2 indicates Parkinsonism inheritance.

6. The method of claim 5, comprising diagnosing said subject as having Parkinsonism inheritance if said polynucleotide comprises an A at position 6055 of SEQ ID NO:2.

7. The method of claim 5, wherein said sample is a blood sample.

* * * * *

UNITED STATES PATENT AND TRADEMARK OFFICE
CERTIFICATE OF CORRECTION

| | | |
|---|---|---|
| PATENT NO. | : 7,993,841 B2 | Page 1 of 1 |
| APPLICATION NO. | : 12/433385 | |
| DATED | : August 9, 2011 | |
| INVENTOR(S) | : Jan O. Aasly | |

It is certified that error appears in the above-identified patent and that said Letters Patent is hereby corrected as shown below:

<u>35 U.S.C. §103</u>

Column 1 (Inventors), line 2, please delete "MN" and insert --FL--, therefor.

Column 39, lines 37-38 (Claim 1), please delete "to be screened for Parkinsonism inheritance".

Signed and Sealed this
Seventh Day of February, 2012

David J. Kappos
*Director of the United States Patent and Trademark Office*